United States Patent
Wang et al.

(10) Patent No.: US 12,049,662 B2
(45) Date of Patent: Jul. 30, 2024

(54) RAPID ANTIMICROBIAL SUSCEPTIBILITY TESTING BY VIDEO-BASED OBJECT SCATTERING INTENSITY DETECTION

(71) Applicant: ARIZONA BOARD OF REGENTS ON BEHALF OF ARIZONA STATE UNIVERSITY, Scottsdale, AZ (US)

(72) Inventors: Shaopeng Wang, Chandler, AZ (US); Fenni Zhang, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 17/590,457

(22) Filed: Feb. 1, 2022

(65) Prior Publication Data

US 2022/0243246 A1   Aug. 4, 2022

Related U.S. Application Data

(60) Provisional application No. 63/144,207, filed on Feb. 1, 2021.

(51) Int. Cl.
  *C12Q 1/06* (2006.01)
  *C12Q 1/18* (2006.01)
  *G06T 7/00* (2017.01)
  *G06T 7/246* (2017.01)

(52) U.S. Cl.
  CPC ............... *C12Q 1/06* (2013.01); *C12Q 1/18* (2013.01); *G06T 7/0016* (2013.01); *G06T 7/246* (2017.01); *G06T 2207/10056* (2013.01); *G06T 2207/30024* (2013.01); *G06T 2207/30241* (2013.01)

(58) Field of Classification Search
  None
  See application file for complete search history.

(56) References Cited

U.S. PATENT DOCUMENTS

| | | | |
|---|---|---|---|
| 2007/0159627 A1* | 7/2007 | Johnson | G01N 15/1459 356/335 |
| 2014/0278136 A1* | 9/2014 | Shamsheyeva | C12Q 1/18 702/19 |
| 2016/0161404 A1 | 6/2016 | Marshall et al. | |
| 2017/0175161 A1 | 6/2017 | Turner | |

FOREIGN PATENT DOCUMENTS

| | | | |
|---|---|---|---|
| CN | 103903278 A * | 7/2014 | |
| WO | WO-2015026794 A1 * | 2/2015 | G01N 15/06 |

OTHER PUBLICATIONS

Delibasis, K. et al. 2020. Measurement and modeling of microbial growth using timelapse video. Sensors 20(2545): 1-17; specif. p. 1 (Year: 2020).*

EngMT. Qu, J. et al. Moving target detection and tracking system. Chinese Patent Application Publication No. CN103903278A, Publication Date: Jul. 2, 2014, pp. 1-74; specif. pp. 1, 2, 4, 5, 6, 48, 52 (Year: 2014).*

Ioannou, M.S. et al. 2015. DENND2B activates Rab13 at the leading edge of migrating cells and promotes metastatic behavior. Journal of Cell Biology 208(5): 629-648; specif. pp. 630, 645 (Year: 2015).*

* cited by examiner

*Primary Examiner* — Adam Weidner
*Assistant Examiner* — Sharon M. Papciak
(74) *Attorney, Agent, or Firm* — MH2 TECHNOLOGY LAW GROUP, LLP

(57) ABSTRACT

Provided herein are methods of assessing the presence of microbes in a liquid sample that include assessing an initial integrated scattering intensity of objects ($I_{C0}$) in the sample and an integrated scattering intensity of the objects at a time t ($I_{Ct}$) from modified images of the liquid sample, and identifying the sample as comprising microbes for ($I_{Ct}$)/($I_{C0}$) above a predefined infection threshold $T_I$. Related systems and other aspects are also provided.

11 Claims, 20 Drawing Sheets

RAPID ANTIMICROBIAL SUSCEPTIBILITY TESTING BY VIDEO-BASED OBJECT SCATTERING INTENSITY DETECTION

CROSS-REFERENCE TO RELATED APPLICATIONS

This application claims the benefit of U.S. Provisional Application No. 63/144,207 filed Feb. 1, 2021, the disclosure of which is incorporated herein in its entirety.

STATEMENT OF GOVERNMENT INTEREST

This invention was made with government support under R01 AI138993 awarded by the National Institutes of Health. The government has certain rights in the invention.

TECHNICAL FIELD

This invention relates to rapid antimicrobial susceptibility testing by video-based object scattering intensity detection.

BACKGROUND

The misuse and overuse of the broad-spectrum antibiotics has led to worldwide development of antimicrobial resistance, posing huge threat to public health. Multidrug resistance bacteria are also identified in many healthcare settings, leading to a wide range of acute infections with high mortality rates. Each year, resistant infections cause millions of hospitalizations and tens of thousands of deaths in the US alone. Urinary tract infections (UTIs) are a frequent bacterial infection in the outpatient setting, affecting many women during their lifetime. Although many UTIs can be uncomplicated, they can also turn into life-threatening infections such as sepsis. The problem can be aggravated by the empirical prescription of the antibiotics for UTI treatment. Current standard methods for both identification and antibiotic susceptibility tests (AST) are slow, typically taking 2-4 days for results to be reported to the patient. Standard methods for UTI screening and AST are culture based, typically taking 48 h or more to produce results, while dipstick tests and manual microscopy are faster but less reliable.

Various emerging rapid AST technologies have been developed using either genotypic or phenotypic approaches. The former detects genes responsible for conferring drug resistance, which is powerful but requires prior knowledge of the genes. Genotypic approaches are nucleic acid amplification testing (NAT)-based detection, which requires a series of sample preparation steps and use of primers and enzymes. Phenotypic AST technologies usually detect phenotypic features (e.g., bacterial size, length, number and morphology) for direct bacterial cell growth measurement, among which, optical detection, including real time microscopy, live cell imaging, flow cytometry and scattering microscopy, have been playing a leading role for rapid assay development. However, most of these technologies only work with pure cultured sample or clinical isolates. Without sample purification and enrichment, very few bacteria can be imaged in high magnification optics, while the single cell imaging with microfluidics is confronted with critical issues such as clogging, bubbles formation, and precise fluid management for real sample test.

SUMMARY

This disclosure describes systems and methods for point-of-care antimicrobial susceptibility testing (AST) with a low-magnification solution scattering imaging system and a real time video-based object scattering intensity detection method. In particular, these systems and methods provide fast AST with free solution forward scattering imaging that works directly on clinical samples in a cuvette without microfluidics. The effect of antibiotics on bacteria growth rate is quantified by a background-free video-based Object Scattering Intensity Detection method (referred as OSID-AST). This method detects the total light intensity scattered from the sample. Real-time imaging allows removal of background noise and tracking of only the scattered light from the moving bacterial cells and particles in the sample, thus providing accurate information on the responsiveness of cells to antibiotics added to clinical urine samples. These systems and methods provide a rapid, affordable, and sensitive detection platform that can significantly reduce the time needed for antibiotic susceptibility determination and enable optimized, targeted therapy in point-of-care settings.

The optical setup and principle of the OSID-AST is described, validated, and applied. The low magnification optics (1-2×) provide a sufficient imaging volume for direct imaging of bacteria in raw samples, avoiding the time-consuming process of culture-based bacteria enrichment. Scattering intensity from moving bacteria and particles in the sample is obtained by subtracting both spatial and temporal background from a short video. The time profile of scattering intensity is correlated with bacteria growth rate and response to antibiotic treatments. Compared to image-based bacteria tracking and counting methods, this imaging processing method accommodates a wider range of bacteria concentrations, simplifies sample dilution processes, and reduces the computational cost of signal processing, which allows real-time signal readout and eases the implementation of multiplexed detection.

Minimal sample preparation and real-time signal readout are advantageous for point-of-care AST applications. To establish the method, 130 clinical urine samples were tested, and the results demonstrated an accuracy of ~92% within 60-90 min for urinary tract infection (UTI) diagnosis, and rapid AST of 55 positive clinical samples with 100% categorical agreement with both the clinical culture result and the parallel agar plating validation results. This technology provides opportunities for prompt infection diagnosis and accurate antibiotic prescriptions in point-of-care settings.

According to an exemplary embodiment, provided herein is a method of assessing the presence of microbes in a liquid sample. The method comprises: directing light from a light source toward a reservoir containing the liquid sample; obtaining, with a camera, a series of images of the liquid sample over a length of time, wherein incident light from the light source is prevented from directly entering the camera, and objects in the liquid sample appear as bright spots in the images of the sample; removing background noise from the images of the liquid sample to yield modified images of the sample; assessing, from the modified images of the liquid sample, an initial integrated scattering intensity of the objects ($I_{C0}$) and an integrated scattering intensity of the objects at a time t ($I_{Ct}$); and identifying the sample as comprising microbes for ($I_{Ct}$)/($I_{C0}$) above a predefined infection threshold $T_I$. According to an exemplary embodiment, the sample comprises microbes, and the method further comprises: treating a portion of the sample with an antibiotic to yield a treated liquid sample; directing light from the light source or an additional light source toward an additional reservoir containing the treated liquid sample; obtaining, with the camera or an additional camera, a series of images of the treated liquid sample over the length of time, wherein incident light from the light source or the additional light source, respectively, is prevented from directly entering the camera or the additional camera, respectively, and objects in the treated liquid sample appear as bright spots in the images of the treated liquid sample; removing background noise from the images of the treated liquid sample to yield modified images of the treated liquid sample; assessing, from the modified images of the treated liquid sample, a change in integrated scattering intensity of the objects in the treated liquid sample from time $t_1$ to time $t_2$ ($\Delta I_{ABX} = I_{ABXt1} - I_{ABXt2}$); and assessing, from the modified images of the liquid sample, a change in integrated scattering intensity of the objects in the sample from time $t_1$ to time $t_2$ ($\Delta I_C = I_{Ct1} - I_{Ct2}$). According to an exemplary embodiment, the method further comprises identifying the microbes as resistant to the antibiotic for a ratio of $\Delta I_{ABX}$ to $\Delta I_C$ that exceeds a predefined resistant threshold $T_R$. According to an exemplary embodiment, the method further comprises identifying the microbes as susceptible to the antibiotic for a ratio of $\Delta I_{ABX}$ to $\Delta I_C$ that is less than or equal to a predefined resistant threshold $T_R$. According to an exemplary embodiment, the microbes comprise bacteria. According to an exemplary embodiment, the liquid sample comprises urine. According to an exemplary embodiment, the camera comprises a video camera. According to an exemplary embodiment, the length of time is at least 60 minutes. According to an exemplary embodiment, the light source comprises a light emitting diode (LED). According to an exemplary embodiment, removing the background noise comprises removing static background noise, dynamic background noise, and local spatial background noise. According to an exemplary embodiment, a volume of the liquid sample is in a range between 1 µL and 10 µL. According to an exemplary embodiment, the method further comprises magnifying the objects in the liquid sample in a range of 1X-5X before obtaining the series of images. According to an exemplary embodiment, the method further comprises maintaining a temperature of the liquid sample between about 35° C. and about 37° C. while obtaining the series of images. According to an exemplary embodiment, the method further comprises, before removing the background noise, averaging a number of sequential images in the series of images, thereby reducing the number of images before removing the background noise from the images. According to an exemplary embodiment, provided herein is a dual-channel imaging apparatus, each channel of the dual channel imaging apparatus comprising: a light source; a first lens assembly comprising a beam block positioned between two biconvex lenses; a sample holder; a camera; and a second zoom lens assembly positioned between the sample holder and the camera, wherein the second lens assembly is configured to provide 1X-5X magnification of a sample in the sample holder to the camera. According to an exemplary embodiment, the light source comprises a light emitting diode (LED). According to an exemplary embodiment, the beam block is configured to prevent incident light from the light source from directly entering the camera. According to an exemplary embodiment, the camera is a video camera. According to an exemplary embodiment, the second lens assembly is configured to provide 1X-5X magnification of the sample in the sample holder to the camera. According to an exemplary embodiment, wherein the sample holder is configured to hold a sample having a volume in a range of 1 µL to 100 µL. The details of one or more embodiments of the subject matter of this disclosure are set forth in the accompanying drawings and the description. Other features, aspects, and advantages of the subject matter will become apparent from the description, the drawings, and the claims..

DETAILED DESCRIPTION

As described herein, a background-free video-based Object Scattering Intensity Detection method for antimicrobial susceptibility testing (OSID-AST) is a low-zoom video-based object scattering imaging detection technique for rapid detection of bacterial infection and determination of antimicrobial susceptibility directly in clinical urine samples. Bacteria like object scattering intensities were obtained by removing the video background with simple spatial and temporal filters, and were used to quantify the growth of the bacterial cells with high sensitivity within 60-90 min. The scattering intensities correlate with both bacteria size and number changes, and are more sensitive than bacterial cell counting with a dynamic range two orders of magnitude wider. The method was first tested with pure *E. coli* cultures and achieved direct AST for stationary phase bacteria in 60 min. The technique was then applied to 130 clinical urine samples and accurately predicted 91.5% of the clinical test identified infection-positive samples within 90 min. AST was also performed on these patient samples with ciprofloxacin and achieved 100% categorical agreements with the clinical lab results within 90 min. Techniques described herein can test raw clinical samples without overnight culturing and can detect object scattering intensity in real time for point-of-care AST. In summary, OSID-AST simplifies sample preparation and testing procedures, improves precision, and greatly shortens the sample to result measurement time. As the object intensity quantifies the bacterial cell grow induced size and number change, which are intrinsic phenotypic feature for AST, the technique is understood to be suitable for applications beyond UTIs.

Figures 1A, 1B, 1C:
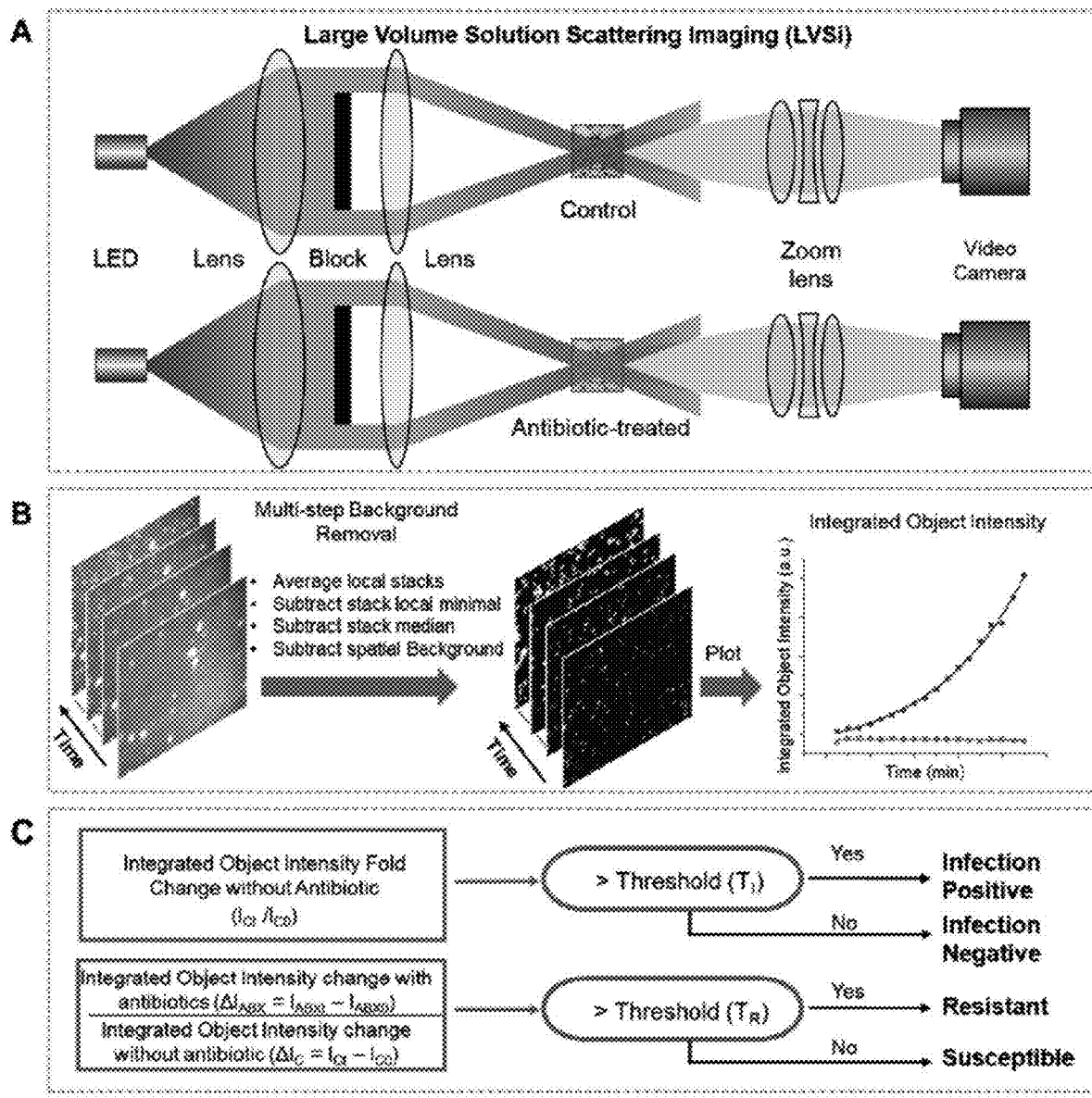
FIG. 1A is a schematic illustration of a dual-channel experimental setup for video-based solution scattering imaging of clinical samples as described herein.
FIG. 1B shows a multi-step image processing for background removal and integrated object intensity plotting.
FIG. 1C shows clinical decision determination based on integrated object scattering intensity.

FIG. 1A is a schematic illustration of a dual-channel experimental setup for video-based solution scattering imaging of clinical samples as described herein. FIG. 1B shows a multi-step image processing for background removal and integrated object intensity plotting. FIG. 1C shows clinical decision determination based on integrated object scattering intensity. $I_{Ct}$ is the integrated object scattering intensity of samples without antibiotics at time t, $I_{C0}$ is the initial intensity of the same sample. $\Delta I_C = I_{Ct} - I_{C0}$ and $\Delta I_{ABX} = I_{ABXt} - I_{ABX0}$, represent the integrated object scattering intensity change at time t for antibiotic-untreated (control) and -treated samples, respectively.

To minimize the sample pre-process time, a low magnification solution forward scattering imaging with dark field illumination is provided for direct real sample detection, and an efficient background removal algorithm for rapid AST based on object scattering intensity (FIG. 1).

FIG. 1A depicts a dual channel image system configured to measure an antibiotic treated sample simultaneously with an untreated sample as control. The system uses a forward scattering geometry to minimize image intensity blinking associated with the rotation of cells in the solution. Furthermore, a beam block prevents the incident light from directly entering the camera, enabling high contrast and low background dark field images of the bacterial cells. Bacterial cells, as well as similar size particles, in a liquid sample are imaged as individual bright spots, which move slowly due to thermal drift, as the sample is heated from bottom to keep it at 37° C. Videos of the control and antibiotic-treated sample are recorded. An automated image processing protocol described in FIG. 1B removes background noises in both the videos of the control and antibiotic-treated sample. In an example of this protocol, the raw video stacks (e.g., 1 min duration, 10 fps) are averaged for every 4 frames to increase signal to noise ratio and to reduce data size. The static and slow drifting background noises from cuvette defects scattering and cuvette wall reflection are removed with temporal local minimal subtraction of each pixel for every 10 frames. The dynamic background noise caused by thermal and mechanical drift induced moving reflection and scattering is mostly removed by subtracting the whole stack temporal median image. The remaining background is removed by subtracting the local spatial background calculated by rolling ball average with radius of 10 pixels for all pixels in the image. The typical computational time for processing a 1 min video is only ~45 seconds with a desktop personal computer. Other protocols can be used. After background removal, the video intensity is typically dominated by the object intensity of all particles including both bacterial cells and non-bacterial particles. Since the non-bacterial particle intensity is stable over time, the change of the object scattering intensity is correlated with bacterial growth rate.

The integrated object scattering intensity quantification enables detection of bacterial infection and AST for infection positive samples with an algorithm such as that depicted in FIG. 1C. Two test solutions are prepared from a patient's sample. One solution with medium and antibiotics for AST and the other one with medium only as control. To detect bacterial infection, the integrated object scattering intensity in the control group is quantified over time (e.g., the object scattering intensity is measured every 5 min with the 1 min video and for a total of 90 min). Clinical decision determination is based on integrated object scattering intensity. $I_{Ct}$ is the integrated object scattering intensity of samples without antibiotics at time t, $I_{C0}$ is the initial intensity of the same sample. $\Delta I_C = I_{Ct} - I_{C0}$ and $\Delta I_{ABX} = I_{ABXt} - I_{ABX0}$, represent the integrated object scattering intensity change at time t for antibiotic-untreated (control) and -treated samples, respectively. If the fold increase of integrated object intensity over initial value ($I_{Ct}/I_{C0}$) is above an infection threshold ($T_I$), or $I_{Ct}/I_{C0} > T_I$, the sample is identified as infection positive. Otherwise, the sample is determined as infection negative. For antibiotic resistance detection, the integrated object intensity change over time in the raw sample ($\Delta I_C = I_{Ct} - I_{C0}$)

and in the antibiotic treated sample ($\Delta I_{ABX}=I_{ABXt}-I_{ABX0}$) are calculated. If the ratio between the two ($\Delta I_{ABX}/\Delta I_C$) is above a resistant threshold ($T_R$), or $\Delta I_{ABX}/\Delta I_C > T_R$, which indicates insufficient bacterial inhibition by the antibiotic, the sample is identified as resistant. If the ratio is at or below $T_R$, bacteria growth is inhibited by the antibiotic, and the sample is defined as susceptible to that antibiotic.

Testing OSID-AST with Pure *E. coli* and *S. saprophyticus* Cultures

Figures 2A, 2B:
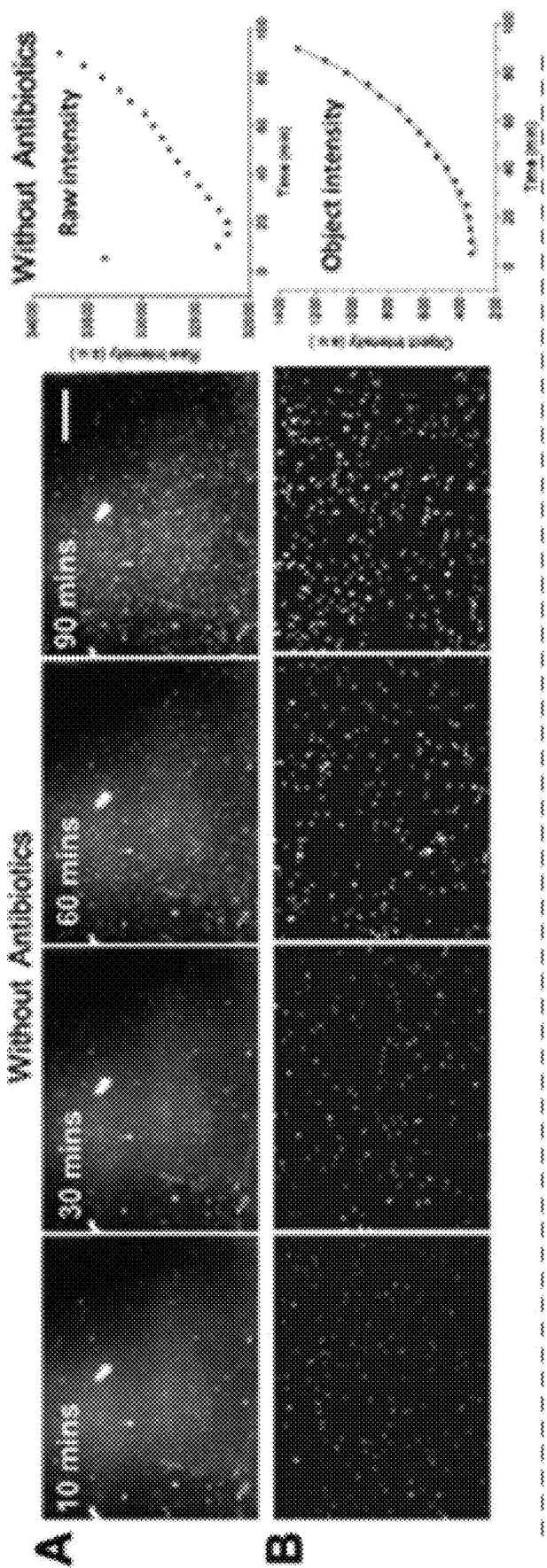
FIGS. 2A-2D show integrated scattering intensity detection of antibiotic susceptible *E. coli*. Pure *E. coli* culture without antibiotics: snapshots of cell images at different time points and the corresponding image intensity plot vs time before (FIG. 2A) and after multi-step background removal (FIG. 2B). Pure *E. coli* culture with antibiotics (32 µg/ml nitrofurantoin): snapshots of cell images at different time points and the corresponding image intensity plot vs time before (FIG. 2C) and after multi-step background removal (FIG. 2D). Scale bar, 400 µm.
Figures 2C, 2D:
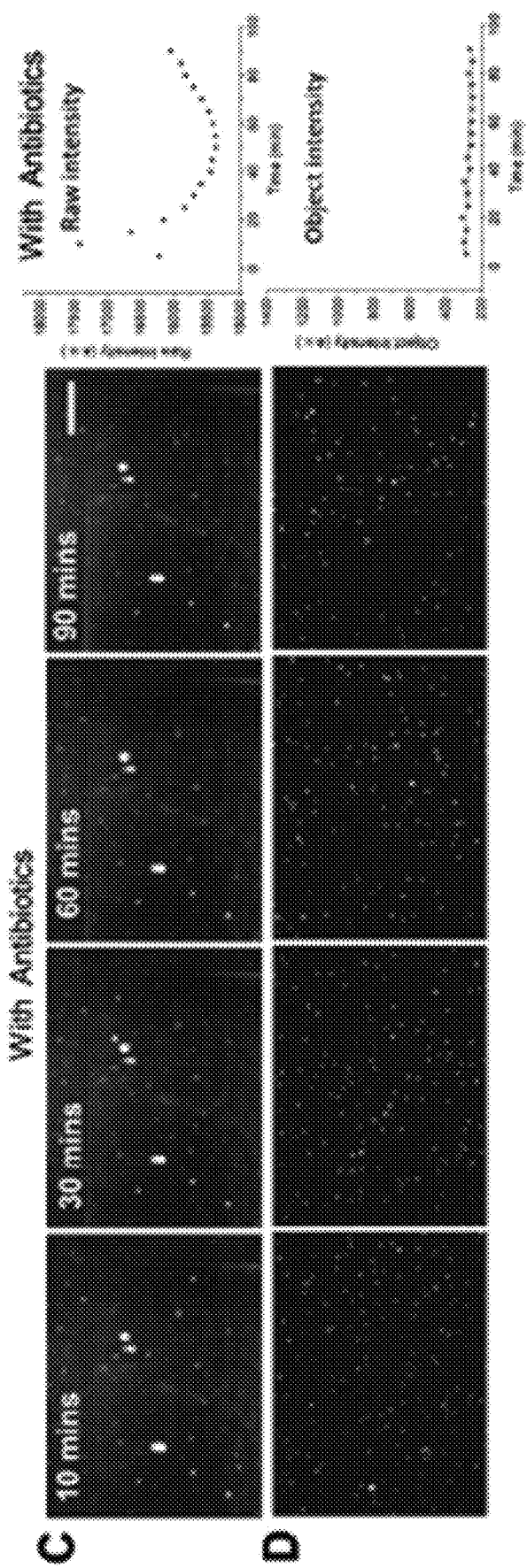
Figures 3A, 3B:
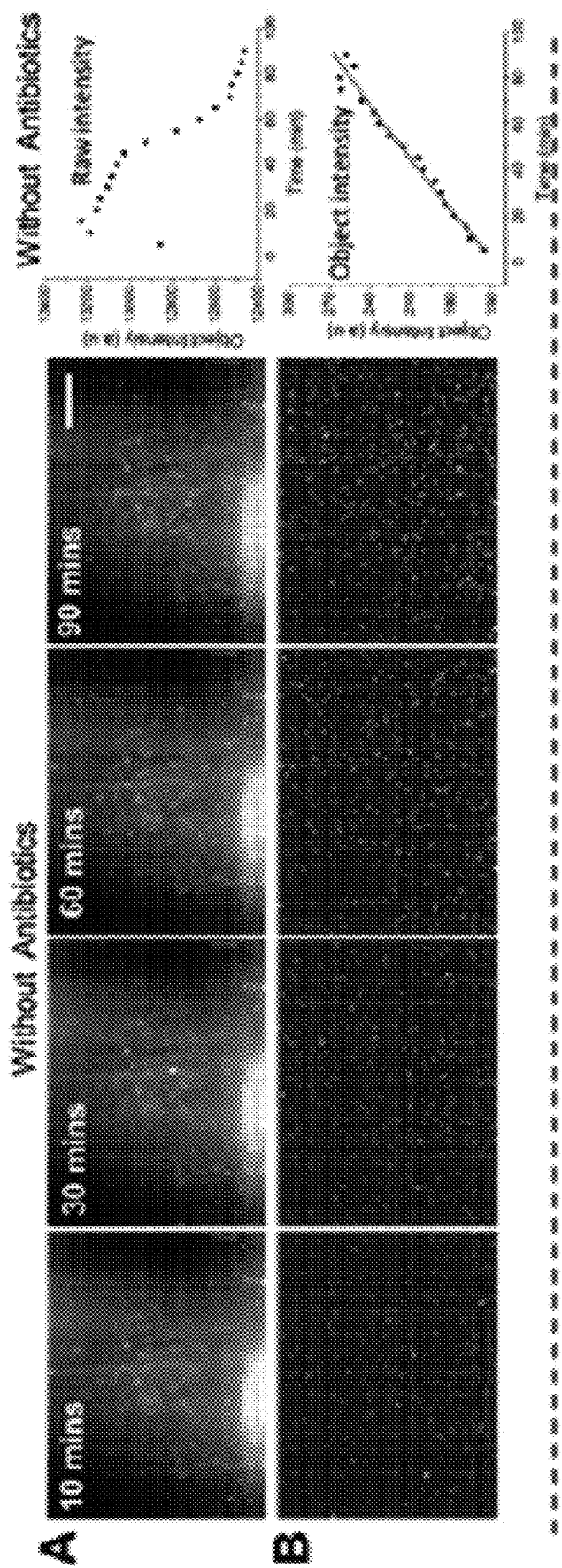
FIGS. 3A-3D show integrated scattering intensity detection of antibiotic susceptible *S. saprophyticus*. Pure *S. saprophyticus* culture without antibiotics: snapshots of cell images at different time points and the corresponding image intensity plot vs time before (FIG. 3A) and after multi-step background removal (FIG. 3B). Pure *S. saprophyticus* culture with antibiotics (2 µg/ml ciprofloxacin): snapshots of cell images at different time points and the corresponding image intensity plot vs time before (FIG. 3C) and after multi-step background removal (FIG. 3D). Scale bar, 400 µm.
Figures 3C, 3D:
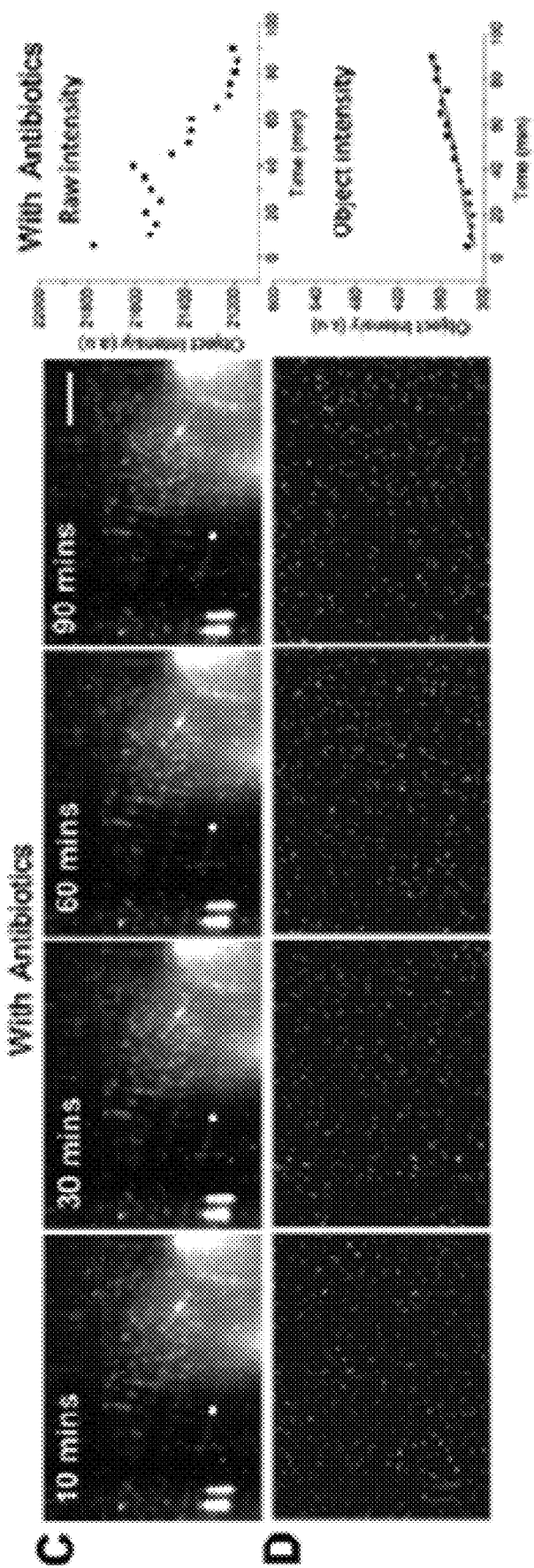

To establish the method, *E. coli* and *S. saprophyticus* cultures (see Materials and Methods) with and without antibiotics were imaged for bacteria growth measurements. *E. coli* is the most predominant pathogen causing 60-80% of community-acquired UTIs, while *S. saprophyticus* is the second-most common cause of community-acquired UTIs (10-20%). To mimic the real sample condition and speed up AST, *E. coli* and *S. saprophyticus* stationary phase cultures in fresh culture medium were used without additional subculture. The individual bacterial cells were imaged as bright spots moving dynamically in the video. The integrated object intensity of all cells was quantified with a 1 min duration video in every 5 min interval for a total of 90 min after real-time background removal processing. The bacteria growth curves of both control and antibiotic-treated sample were plotted for antibiotic susceptibility determination The object intensity detection and the raw intensity detection for antibiotic susceptibility testing with pure *E. coli* cultures were compared. The raw intensity detection is similar to the traditional optical scattering measurement with spectrometry. In the absence of antibiotics, *E. coli* multiplies over time as indicated by the increase in both the raw intensity and integrated object intensity (FIGS. 2A and 2B). However, the raw video presents obvious background noises including both static and dynamic optical background contributed from residual background illumination, scattering from defects and dust on the cuvette wall, and ghost light (FIG. 2A), which interfere with the intensity increase induced by *E. coli* growth. In contrary, after background removal, the intensity changes are more evident as the bacterial cell scattered light dominates in the video (FIG. 2B). To accurately track *E. coli* growth, the averaged intensity of a 1 min video was quantified in every 5 min. With the raw video intensity, *E. coli* growth was detected in 90 min, but the growth curve does not show obvious exponential increase and the intensity increase is small compared with the initial background intensity. The growth curve plotted with the integrated object intensity shows more evident exponential growth (FIG. 2B). Similarly, for the antibiotic-treated sample (32 µg/ml nitrofurantoin), the raw video show obvious background noises, and the raw intensity show a fluctuate curve (FIG. 2C) due to drifting background noise. In contrary, the background-free integrated object intensity (FIG. 2D) shows a flat line over time, means no bacteria growth with the present of antibiotics, a clear susceptible result.

Similarly, the object intensity detection and the raw intensity detection for pure *S. saprophyticus* cultures were performed and compared in FIGS. 3A-3D. Unlike *E. coli* cells, *S. saprophyticus* are gram-positive cells that form grape-like clusters during growth and need longer time for reproduction, which only increase the scattered light intensity without number increase. During the 90 min detection, the raw intensity of both control and antibiotic (2 µg/ml ciprofloxacin) treated sample decrease with time as the background noise intensity dominates, which cannot be used for bacterial growth quantification. In contrary, obvious growth was observed with object intensity detection in control sample, with ~1.7 times intensity change, and the antibiotic treated sample also showed intensity increase due to the initial cell elongation, showing ~1.1 times intensity change. As $\Delta I_{ABX}/\Delta I_C = \sim 0.14$, well below the resistance threshold of 0.5, so the *S. saprophyticus* culture is determined as a susceptible sample with OSID-AST.

Figures 4A, 4B, 4C:
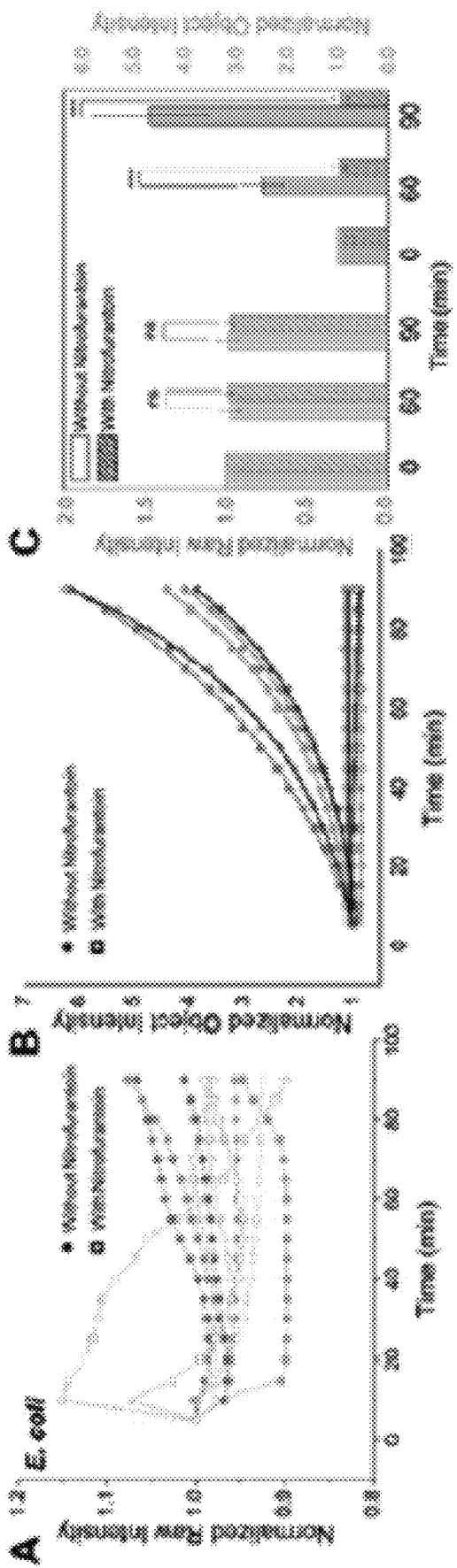
FIGS. 4A-4I show statistical analysis of the integrated object intensity detection for rapid AST with different antibiotics and different bacterial strains. The raw image intensity results of 5 representative tests under 32 µg/ml nitrofurantoin with *E. coli* culture (FIG. 4A), 2 µg/ml ciprofloxacin with *E. coli* culture (FIG. 4D), and 2 µg/ml ciprofloxacin with *S. saprophyticus* culture (FIG. 4G). The integrated object intensity results of the 5 corresponding tests under 32 µg/ml nitrofurantoin *E. coli* culture (FIG. 4B), 2 µg/ml ciprofloxacin with *E. coli* culture (FIG. 4E), and 2 µg/ml ciprofloxacin with *S. saprophyticus* culture (FIG. 4H). The statistical analysis of bacterial growth at different time points under 32 µg/ml nitrofurantoin *E. coli* culture (FIG. 4C), 2 µg/ml ciprofloxacin with *E. coli* culture (FIG. 4F), and 2 µg/ml ciprofloxacin with *S. saprophyticus* culture (FIG. 4I). While raw image intensities show no significant difference between samples with and without antibiotics, the integrated object intensities show significant difference between the two groups after 60 min for both *E. coli* and *S. saprophyticus*. ns: not significant, *: $p<0.01$, : $p<0.005$, *: $p<0.001$.
Figures 4D, 4E, 4F:
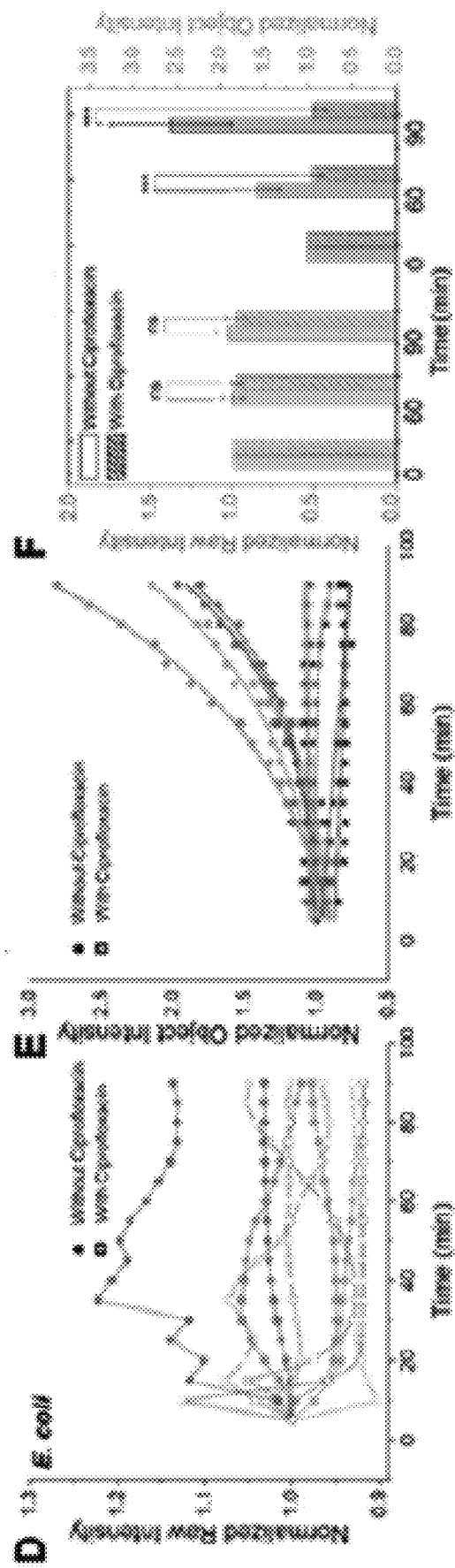
Figures 4G, 4H, 4I:
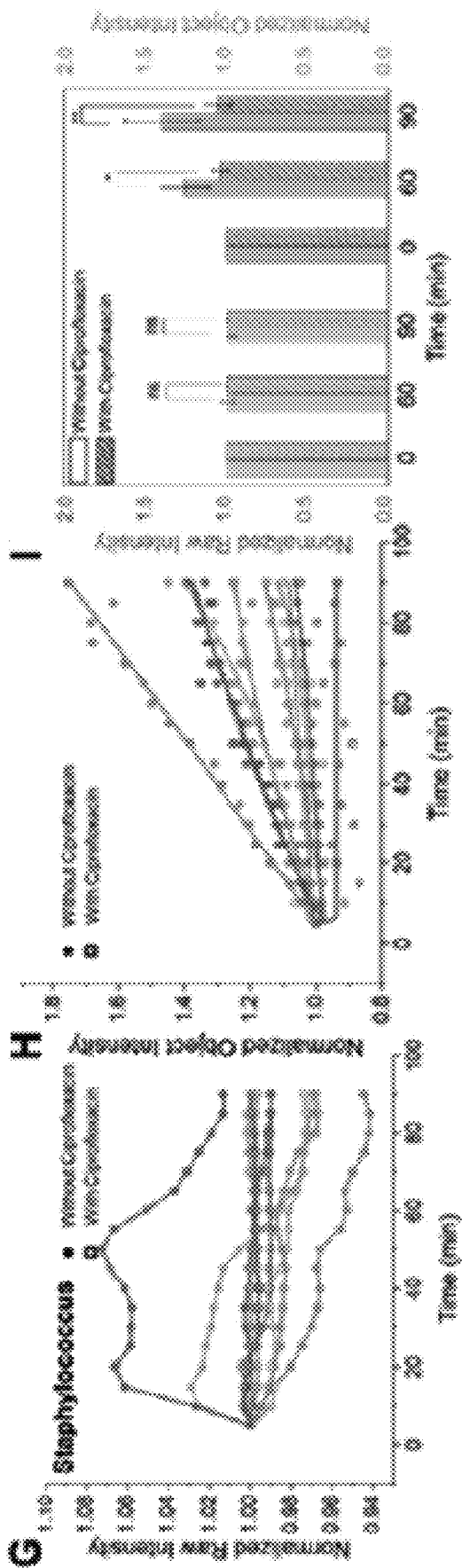

To further validate the robustness of the object intensity detection method, different batches of cultures were tested for statistical comparison. To compare the results from different experiments, both raw intensity and object intensity at each time point were normalized to the initial video intensity to generate the fold increase of cell growth. Five representative results with and without antibiotics are plotted in FIGS. 4A-4C (32 µg/ml nitrofurantoin) and FIGS. 4D-4F (2 µg/ml ciprofloxacin) for *E. coli* culture and FIGS. 4G-4I (2 µg/ml ciprofloxacin) for *S. saprophyticus* culture. In raw video intensity detection, the growth difference between control and antibiotic-treated sample are not significant for *E. coli* under nitrofurantoin (FIG. 4A) and ciprofloxacin (FIG. 4D), and *S. saprophyticus* under ciprofloxacin (FIG. 4G). Large sample to sample variations were observed, making it difficult for antibiotic susceptibility determination. In contrast, for the object intensity detection after background removal, the growth difference between control and antibiotic-treated sample were obvious and consistent among different samples for all antibiotics and both strains. The antibiotic susceptibility of *E. coli* cells can be determined as early as 40 min for nitrofurantoin (FIG. 4B) and 60 min for ciprofloxacin (FIG. 4E). For *S. saprophyticus* cultures, due to a slower growth rate and the object intensity increase in both control and antibiotic treated samples, longer time is needed for antibiotic susceptibility determination. Statistical analysis of all the samples at different time points (0, 60, 90 min) indicates that the inhibition of the bacterial cells can be reliably differentiated with integrated object intensity detection, and the statistical significance increases with time, while the raw intensity detection shows no significant difference between control and the antibiotic treated sample even at 90 min (FIGS. 4C, 4F, and 4I).

The video-based object intensity detection described herein does not need to identify and track individual scattering objects, so it can work with higher density of particles and thus wider range of bacteria concentrations, ranging from $10^4$ to $10^7$ cells/mL (CFU/mL), as long as the raw intensity does not saturate during detection. The wider dynamic range of the object intensity detection enables detecting bacteria in clinical urine samples with a single unified dilution step, which can dramatically simplify the sample preparation process by eliminating the premeasurement of particle concentration and the particle concentration dependent dilution step. In addition, the total AST time decreases with the increase of the bacterial concentration in the working sample. A calibration between *E. coli* concentration and AST time is performed and determined. Furthermore, no manual threshold detection and complicated tracking process is needed in the background removal process, which eliminates artifacts and dramatically reduces the computational cost, allowing fully automated, real time image processing and results reporting. Also, object intensity detection works with more bacterial strains than digital counting.

The integrated object intensity measures both cell size increase and number increase for bacteria growth determination. For antibiotics inhibiting cell growth, such as nitrofurantoin (interferes with the critical enzymes) and ciprofloxacin (inhibits DNA replication), they stop cell growth in both size and number, and the object intensity measurements provide rapid and evident results for AST determination. However, for antibiotics that stop cell dividing but not growth, such as ampicillin, longer detection time is needed for AST determination, as cell elongation also increases the object scattering intensity.

UTI Infection Detection and AST with Clinical Urine Samples

After validation of OSID-AST with pure *E. coli* and *S. saprophyticus* cultures, this method was applied to clinical urine samples for both UTI infection detection and AST of the UTI-causing bacteria. Infection detection measures the integrated object intensity increase over time in the antibiotic free (control) sample. A positive infection is identified when the intensity increase is higher than the infection threshold, which indicates active bacteria growth. AST compares the intensity changes in samples incubated with and without antibiotics. 130 de-identified clinical urine samples collected from hospitalized patients at Mayo Clinic were measured by OSID-AST. The results were validated with parallel agar plating and CFU quantitation for all samples, and compared with clinical lab results measured by BD Phoenix.

Figures 5A, 5B, 5C, 5D:
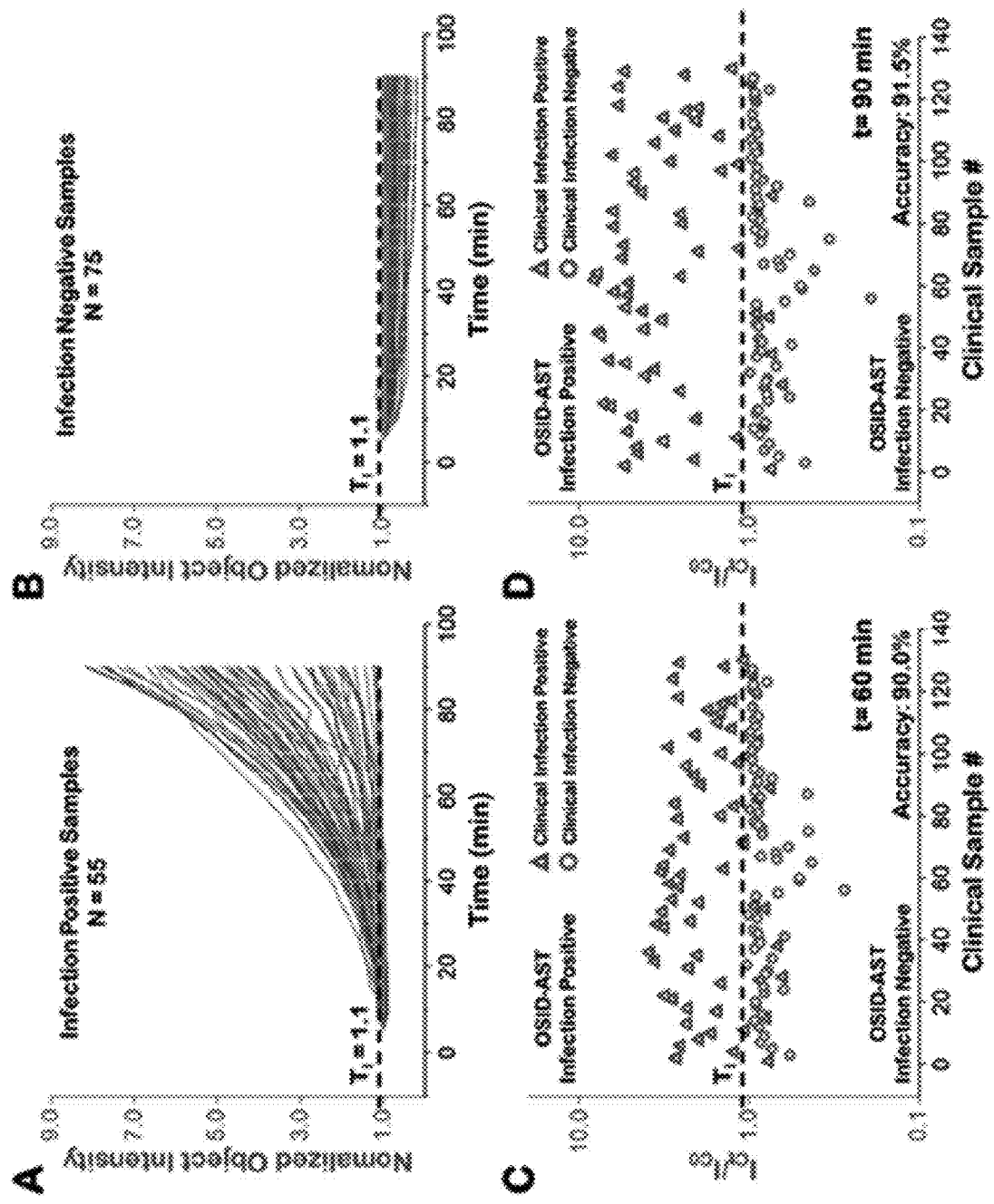
FIGS. 5A-5D show rapid infection detection with 130 clinical urine samples. The normalized integrated object intensity results over 90 min of 55 infection positive clinical samples (FIG. 5A) and 75 infection negative clinical samples (FIG. 5B). Grey circles are individual sample values and the black dot are mean value over all samples. The comparison of reference method (BD Phoenix, black circles are infection positive and red squares are infection negative) and OSID-AST determinations of infection at 60 min (FIG. 5C) and 90 min (FIG. 5D) with infection threshold $T_f = 1.1$.

UTI detection: All 130 clinical urine samples were tested, and samples with UTI were detected (FIGS. 4A-4I). 55 of the 130 clinical samples exhibited significant object intensity increase despite sample-to-sample variability and were identified as infection positive (FIG. 5A), while the rest show minimal object intensity change and were identified as infection negative (FIG. 5B). For cross validation, the normalized integrated object intensity of each sample at time points of 60 min and 90 min (FIGS. 5C and 5D) were compared with the BD Phoenix gold standard method results obtained in the Microbiology Lab at Mayo Clinic, where the samples were collected. At 60 min, the integrated object intensity falls into two separated clusters: one cluster of samples with normalized integrated object intensity bigger than 1 and one cluster of samples with normalized object intensity smaller than 1 (FIG. 5D). The two clusters were further separated with increased incubation times, indicating increasing UTI detection accuracy with time. By setting the infection threshold at 1.1, 75 samples were determined to be infection negative and 55 samples were determined to be infection positive with accuracies that increased from ~90% at 60 min to ~91.5% at 90 min. By the time of 90 min, 11 false negative samples were determined from the 130 samples tested. The parallel microbiological agar plating results shows that these false negative samples have an initial bacteria concentration below 1000 CFU in the prepared testing sample, which is beyond the detection limit of this AST method.

The present LVSi system has an image volume of 5 µL, allowing imaging of sufficient numbers of bacterial cells simultaneously in urine samples at clinically relevant concentrations ($10^4$-$10^7$ CFU). However, when the bacterial concentration is below 1000 cells/mL, less than κ cells can be detected, which needs longer detection time for AST determination. Among the 11 false negative samples, 2 samples were tested negative with the initial on-site plating validation with overnight culturing after the samples transported to the testing site. They likely lost viability during the cold storage and transportation, which could be avoided when measured onsite with fresh urine. The other 9 samples were tested marginal positive with the initial plating (7 out of the 9 samples with concentrations between $10^4$-$10^5$ CFU, and only two of the samples have bacterial concentration higher than $10^5$ CFU), but the parallel plating validation results after all sample handling, including prewarm, filtration and dilutions show low initial counts of bacterial cells (below 1000 cells/ml). Therefore, most of these false negative results (9/11) are due to low initial bacterial concentration and sample handing process, possibly resulting from over filtration or over dilution. These sample were diluted from 10 to 1000 times so that both digital counting and object scattering intensity can be performed. Since OSID-AST can work with a much higher particle concentration range, these false negative results could be avoided with less dilution of the sample and better sample collection and handling process.

Bacterial cell growth was measured with integrated object scattering intensity, which has very low computational cost in data processing and allows automated data processing in real time. The same clinical samples were analyzed with a single cell counting method, which needs extra manual threshold selection for cell detection and tracking processing that prevent fully automated data processing. The single cell counting detection showed 17 false negative samples in the 130 tested samples, with additional 6 false negative samples than the object intensity detection. This is because object intensity measures both size and number increase during cell grow, while cell counting only signals the number increase, and the number increases typically happen later than the size increases. In addition, cell counting is not always accurate with high particle density sample, which need an extra imaging and dilution determination step for each sample. The extra dilution could also lead to false negative result as there are insufficient bacteria in the sample to be measured. Furthermore, the counting method does not typically work with bacterial cells that stay aggregated after division, such as Staphylococcal bacteria in UTI, while the object intensity detection works for all types of bacteria.

Figures 6A, 6B, 6C, 6D:
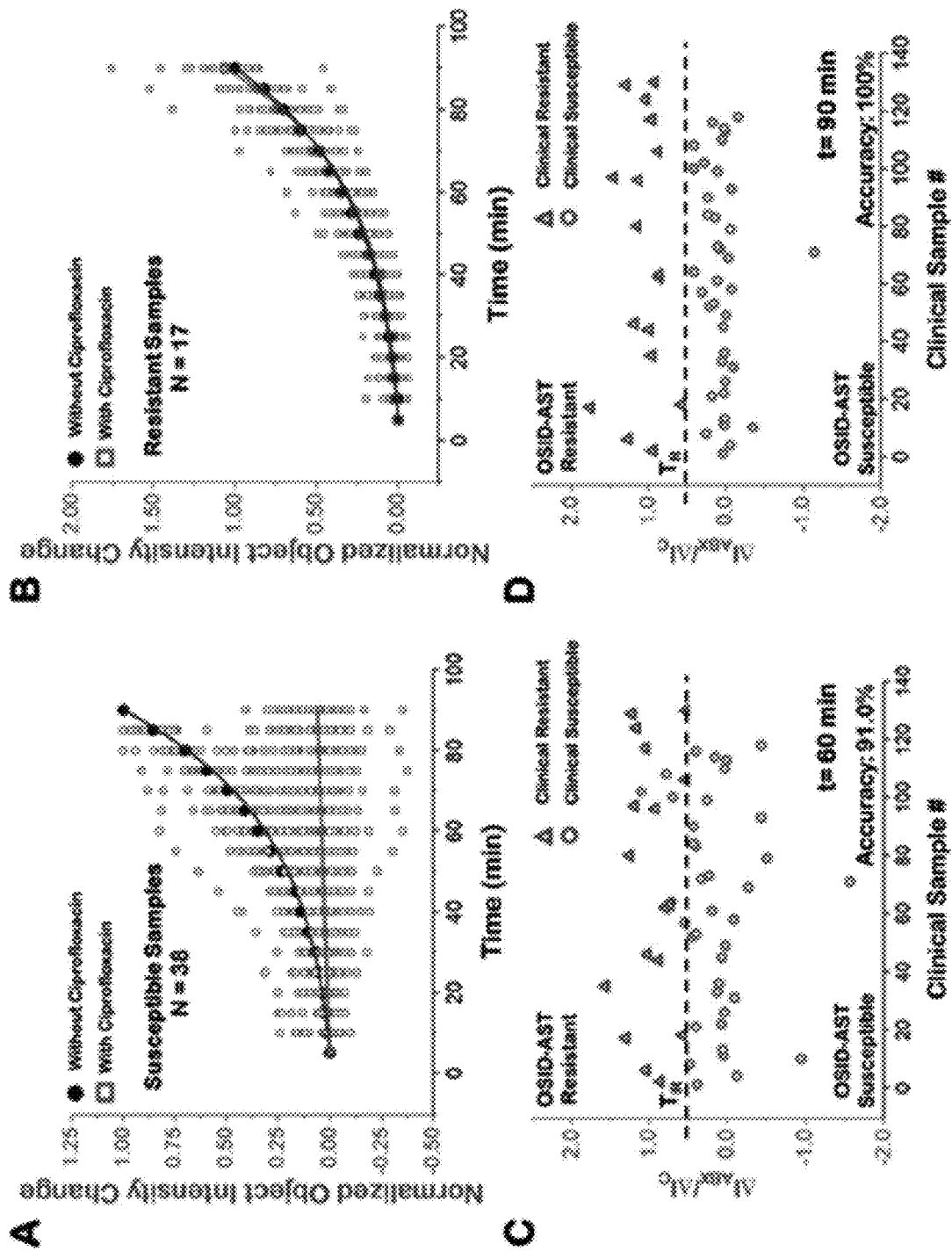
FIGS. 6A-6D show direct AST with infection positive clinical samples. The normalized integrated object intensity increase (normalized by the integrated object intensity at 90 min) over 90 min of all 38 susceptible samples (FIG. 6A) and 17 resistant samples (FIG. 6B). Comparison of reference method (BD Phoenix) and direct AST for susceptibility determination with 60 min detection (FIG. 6C) and 90 min detection (FIG. 6D).
Figures 7A, 7B, 7C, 7D, 7E, 7F, 7G, 7H:
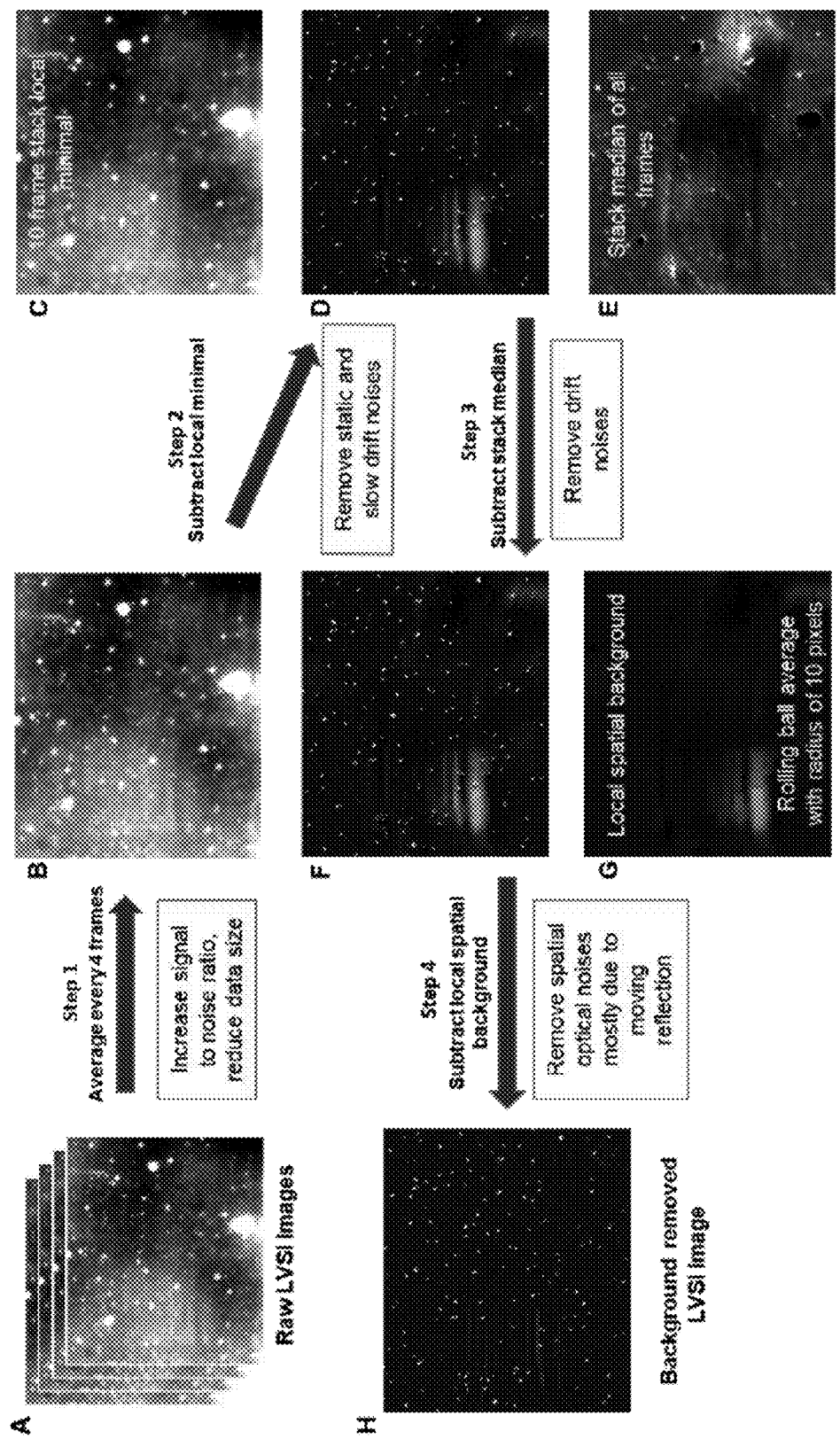
FIGS. 7A-7H show a background removal processing flow chart according to an exemplary embodiment.

Rapid AST: OSID-AST was performed on the 55 UTI positive clinical samples by comparing integrated object intensity change in antibiotic-treated samples ($\Delta I_{ABX}$) with that of the control samples ($\Delta I_C$) following the algorithm defined in FIG. 1C. When $\Delta I_{ABX}$ is consistently lower than $\Delta I_C$, the sample is determined as an antibiotic susceptible sample (FIG. 6A). In contrary, when $\Delta I_{ABX}$ and $\Delta I_C$ values are similar, the sample is identified as a resistant one (FIG. 6B). To explore AST accuracy over time, the susceptibility threshold ($T_S$) is set at 0.5, corresponding to 50% reduction in bacterial cells growth rate, and compared the results with those obtained from reference method (BD Phoenix) (FIGS. 6C and 6D). With the 60-min detection, 5 clinical tested susceptible samples localized within the resistance zone or at the threshold, demonstrating a category accuracy of ~91% (FIG. 6C), while the 90 min detection increased the category accuracy to 100% with 17 samples identified as resistant to ciprofloxacin and the remaining 38 were susceptible (FIG. 6D). These results were in 100% agreement with both BD Phoenix results from clinical microbiology testing and the parallel agar plating validation experiments.

In the protocol described herein, the clinical samples are refrigerated and transported in ice box from the hospital to the lab. To mimic the fresh and warm urine sample, a 30 min prewarm was performed before testing. Next, a simple filtration step was performed to remove large particles in the sample, and then a 1:10 dilution step was performed for nutrient supplementary, which took another 2 minutes for each sample. Therefore, the current total assay time for direct AST in clinical sample includes 30 min sample pre-warming, 2 min sample pre-treatment (filtration/dilution) and 60-90 min video-based object scattering detection. The prewarm step is not needed for fresh urine samples. The sample pre-treatment time can be reduced with improved sample collection device that integrated with a filter. Thus, the total AST time can be as short as ~1 hour with real-time growth curve determination.

EXPERIMENTAL DETAILS

Materials and Methods

Materials. *E. coli* ATCC 25922 and *S. saprophyticus* ATCC 15305 were purchased from American Type Culture Collection (ATCC) and stored at −80° C. in 5% glycerol. Ciprofloxacin and nitrofurantoin were purchased from Sigma-Aldrich. The antibiotic powders were stored in the dark at 2 to 8° C.

Bacterial preparation. *E. coli* and *S. saprophyticus* were grown overnight (~15 h) in Luria-Bertani (LB) broth (per liter: 10 g peptone 140, 5 g yeast extract, and 5 g sodium chloride) and Mueller Hinton Broth (MHB, per liter: 2.0 g beef infusion solids, 1.5 g starch, and 17.5 g casein hydrolysate)) at 37° C. and 150 rpm. *E. coli/S. saprophyticus* cultures were diluted in fresh LB broth/MHB to a concentration ranging from $10^4$~$10^7$ cells/mL. An antibiotic at the standard breakpoint concentration was added to one of two preparations. Each bacterial suspension (70 µL), one with and one without antibiotic, was transferred into a cuvette at 37° C. for imaging.

Clinical urine samples. De-identified excess and residual clinical urine samples were obtained from the clinical microbiology laboratory at Mayo Clinic Hospital, Phoenix, Ariz. (Approved by Mayo Clinic Biospecimen Subcommittee BIO00015462). Clinical urine samples were stored at 4° C. and transported in an insulated box with ice packs. Prior to processing, urine samples were pre-warmed for 30 min at 37° C. and passed through a 5 µm syringe filter (MilliporeSigma, Burlington, MA) to remove large substances. Each urine sample was then supplemented with LB broth to a concentration ranging from $10^4$~$10^7$ particles/mL with and without ciprofloxacin (2 µg/mL, final concentrations). After mixing, diluted samples (70 µL) were transferred to cuvettes (Uvette, Eppendorf, Germany), and subjected to LVSi. A total of 130 urine samples were tested using both object intensity tracking and parallel validating plating. Urine samples were prepared and transferred to researchers in a blinded fashion. Upon completion of all experiments, the VSi-AST and parallel plating results were compared with clinical microbiology culture results from the Mayo Clinic Hospital lab.

LVSi. The dual channel large volume scattering imaging system (FIG. 1A) consists of two 800 mW, 780 nm infrared (IR) LEDs (M780LP1, Thorlabs, Inc., USA), each with collimating and focusing lens and a central blocking aperture to focus a ring-shaped illumination through the sample or the reference cuvettes. Wide-view and deep field depth scattering images were recorded by two CMOS camera (BFS-U3-16S2M-CS, Point Grey Research Inc., Canada) at 10 fps through two variable zoom lenses (NAVITAR 12X, Navitar, USA) with zoom factors set at 2.0× for the sample and reference cuvettes. The image volume was determined by the viewing size and focal depth of the optics. For the experiments described in this study, the viewing volume of 2.5 mm×1.9 mm×1.0 mm was equivalent to 4.8 µL at 2.0× magnifying power. The imaging system was enclosed in a thermally-isolated housing unit with a controlled temperature (37° C.).

Biosafety. All sample preparations and measurements were performed in biosafety level 2 (BSL2) laboratories following an IBC-approved BSL2 protocol.

Video Processing. The automated image processing protocol to remove all background noises in the video has 4 steps (FIG. 1B): Step one, the raw video stacks (1 min duration, 10 fps) are averaged for every 4 frames to increase signal to noise ratio and to reduce data size. The size of local stack average is set to avoid cell motion induced blur. Step two, static and slow drifting background noises from cuvette defects scattering and cuvette wall reflection are removed with pixel level temporal local minimal subtraction for every 10 frames. Temporal local minimal is calculated by project the minimal intensity over time for a small stack for each pixel. The stack size is set to with all bacterial cells moved to avoid signal lost. Step three, dynamic background noise caused by thermal and mechanical drift induced moving reflection and scattering is mostly removed by subtracting the whole stack temporal median image. Stack median is calculated by project the median intensity of each pixel for the entire video stacks. Step four, the remaining background is removed by subtracting the local spatial background calculated by rolling ball average with radius of 10 pixels for all pixels in the image. The radius should be set to at least the size of the largest object that is not part of the background. The typical computational time for processing a 1 min video is only ~45 seconds. After background removal, the video intensity is dominated by the object intensity of all particles including both bacterial cells and particles. The algorithms were implemented using ImageJ software.

Setting thresholds for data interpretation. To determine the infection threshold, the results were evaluated using the receiver operating characteristic (ROC) curve constructed using $I_t/I_0$ as a predictor. From the ROC curve for first 20 clinical samples, of which 10 were positive and 10 were negative, the best infection threshold was determined to be 1.1 with a sensitivity of 100% and a specificity of 100% at a 90-minute testing time. Therefore, the final threshold for infection identification ($T_I$) was set as 1.1 for all samples. The susceptible threshold ($T_S$) was set as 0.5, corresponding to 50% growth inhibition in the antibiotic-treated samples.

Statistical analysis. An unpaired two-sided student t-test was used to compare the group differences. A p value of <0.05 was considered as statistically significant.

To further illustrate, FIGS. 7A-7H show a background removal processing flow chart. Step 1: Raw LVSi images recorded at 10 frames per second (A) are averaged for every 4 frames (B) to reduce noise and data size. The size of local stack average is set to avoid cell motion induced blur. Step 2: Subtract stack local minimal (C) from (B) to remove static and slow drifting background noises (D). Stack local minimal is calculated by project the minimal intensity over time for a small stacks for each pixels. The stack size is set to with all bacterial cells moved to avoid loss of signal. Step 3: Subtract stack median of all frames (E) from (D) to remove drift noises (F). Stack median is calculated by project the median intensity of each pixel for the entire video stacks. Step 4: Subtract local spatial background (G) from (F) to get the background free LVSi image (H). Spatial local background of each pixel in the image is calculated by averaging over a large ball with radius of 10 pixels around the pixel to remove large spatial variations of the background intensities. The radius should be set to at least the size of the largest object that is not part of the background.

ROC Curve for Infection Threshold Determination

To determine the infection threshold, the results were evaluated using the receiver operating characteristic (ROC) curve constructed using $I_{Ct}/I_{C0}$ as a predictor. From the ROC curve for the first 20 samples, of which 10 were positive and 10 were negative from the clinical validation, the infection threshold of 1.1 was determined with a sensitivity of 100% and a specificity of 100% at a 90-minute testing time.

Figure 8:
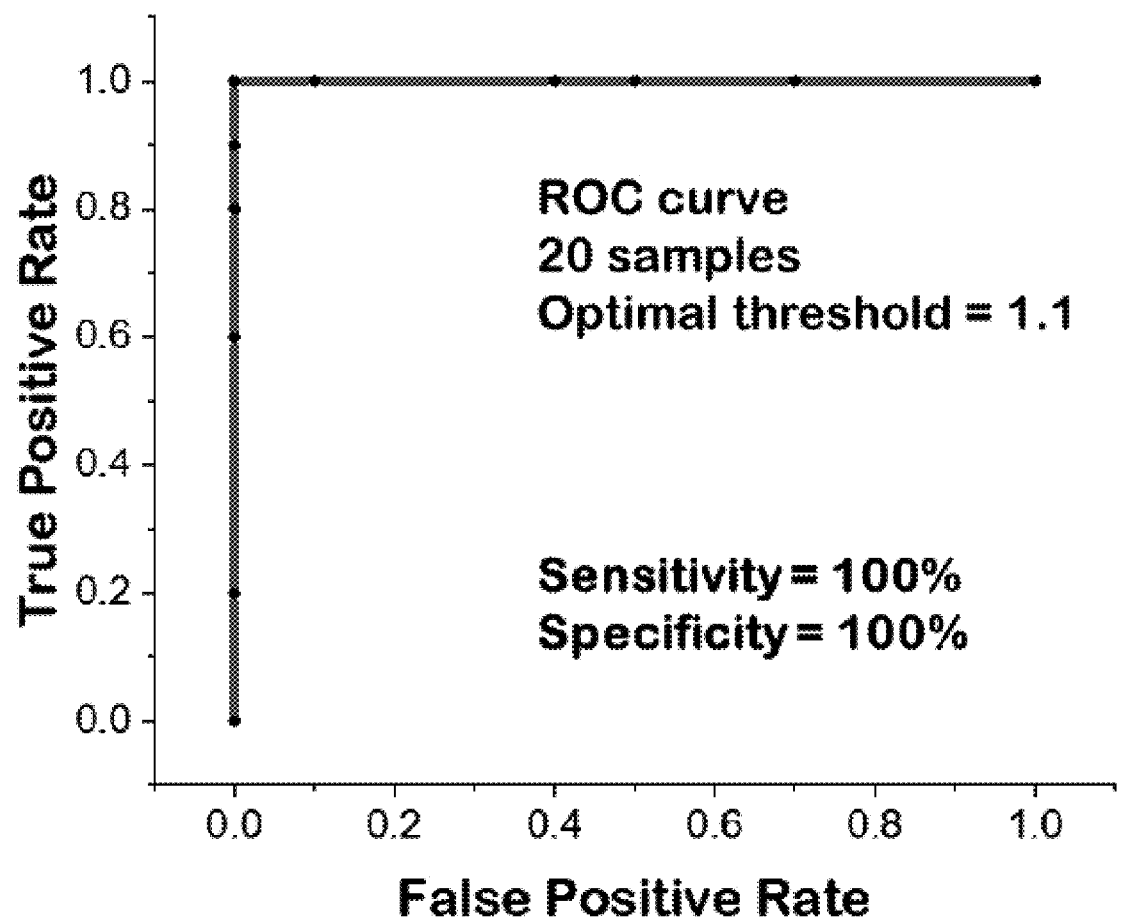
FIG. 8 shows a ROC curve that reveals 100% sensitivity, and 100% specificity at 90 min with threshold of 1.1.
Figures 9A, 9B:
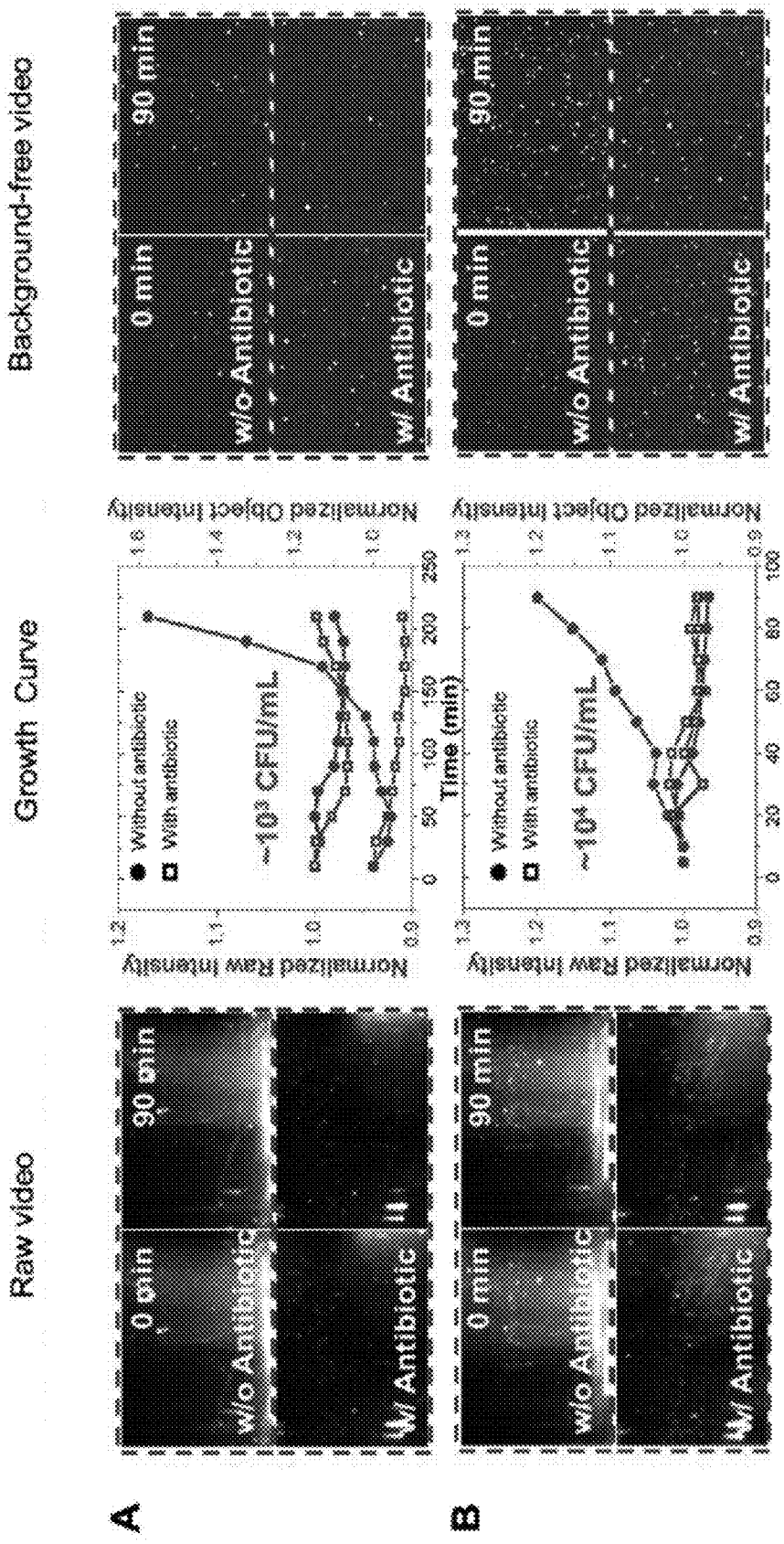
FIGS. 9A-9E show OSID-AST with *E. Coli* cultures of concentrations of $10^3$ (A), $10^4$ (B), $10^5$ (C), $10^6$ (D), $10^7$ (E), respectively.
Figures 9C, 9D:
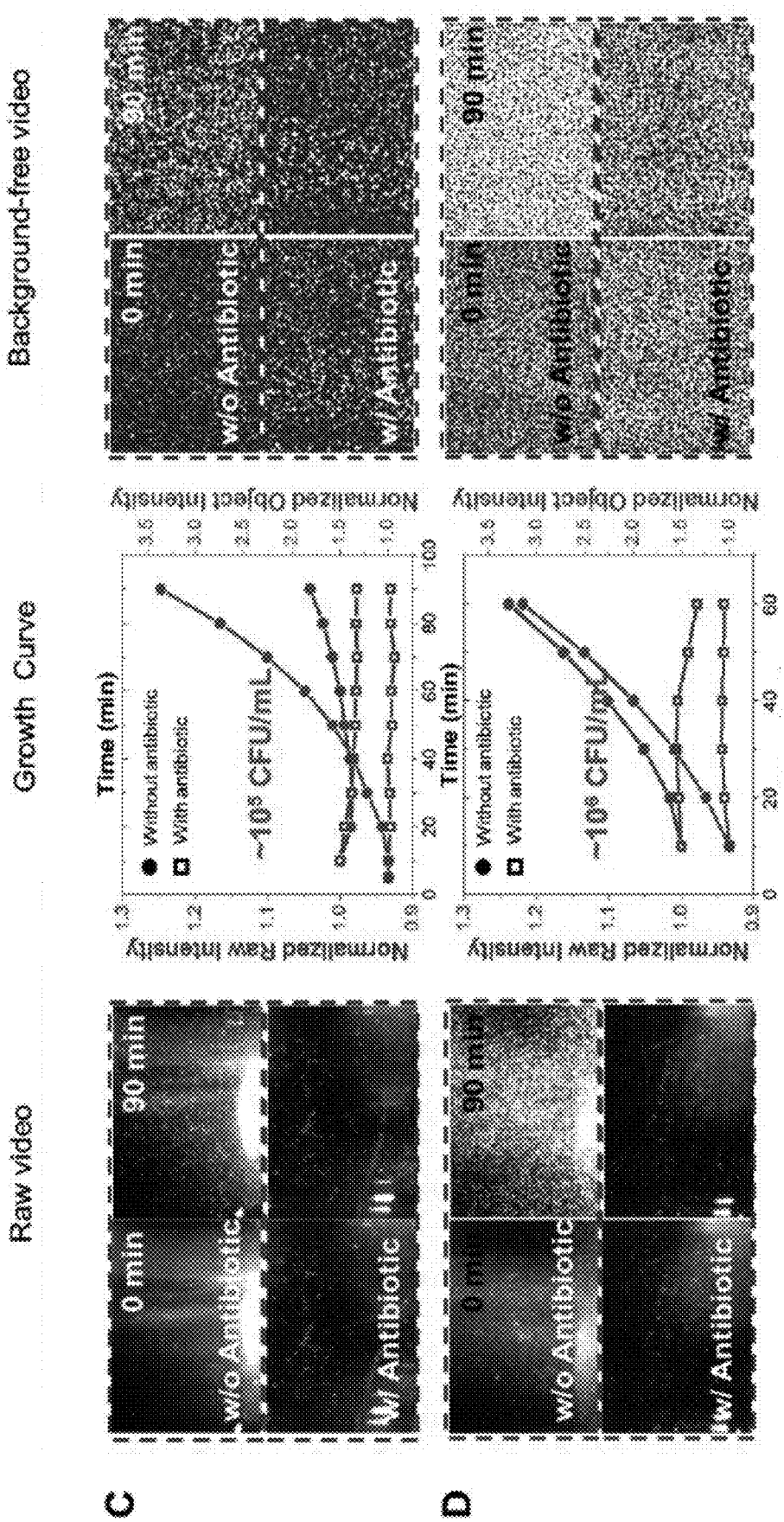
Figure 9E:
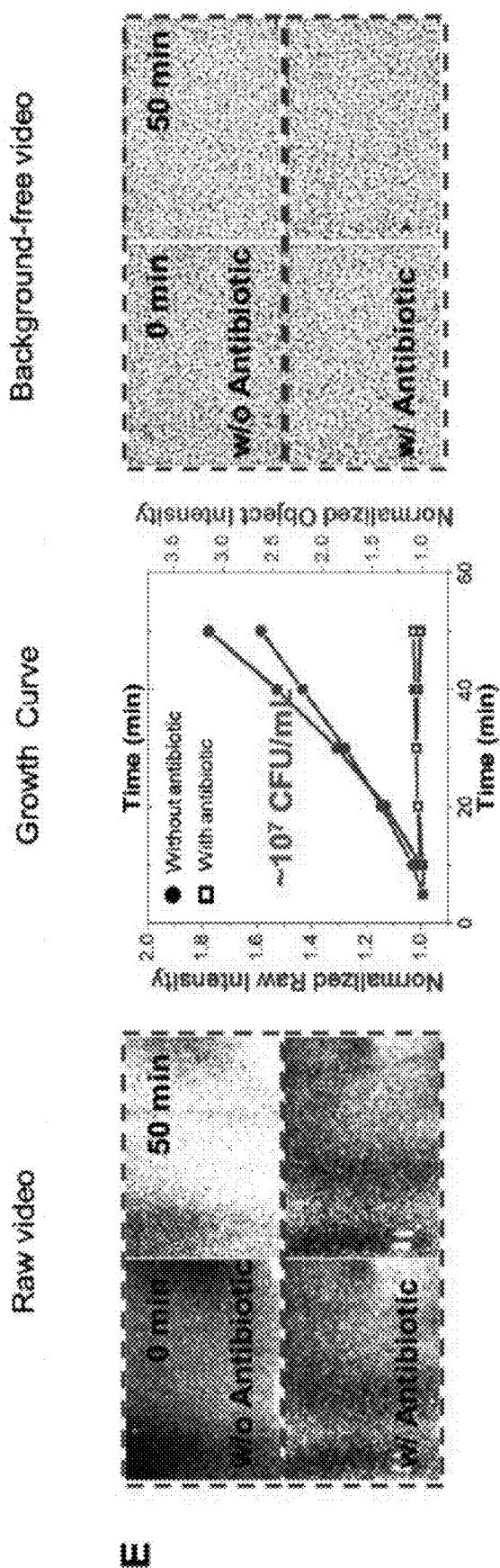

FIG. 8 shows a ROC curve that reveals 100% sensitivity, and 100% specificity at 90 min with threshold of 1.1.

OSID-AST with *E. Coli* Cultures of Different Concentrations

To determine the dynamic range of OSID-AST method, the AST testing was performed with *E. Coli* cultures of different concentrations, ranging from $10^3$ to $10^7$ CFU/ml. The AST results and the corresponding raw intensity and the object intensity are plotted in Figure S3. At the low concentration of $10^3$ CFU/ml, both raw intensity and object intensity result show no obvious increase within 90 min. With longer time testing, the object intensity result shows positive with bacterial infection by the time of 170 min, while raw intensity does not show obvious increase even by the time of 210 min. At the concentrations between $10^4$ and $10^7$ CFU/ml, the object intensity detection works well, and the total AST time decreases with the cell concentrations. Thus, the detection range of object intensity method is between $10^4$ and $10^7$ CFU/ml, while the raw intensity detection only works with high concentrations above $10^6$ CFU/ml. In contrary, the digital counting method needs single cell detection, which only works with low cell concentrations between $10^4$ and $10^5$ CFU/ml. Therefore, OSID-AST works with wider dynamic range, which can further simplify the sample preparation process and provide more robust result.

FIGS. 9A-9E show OSID-AST with *E. Coli* cultures of concentrations of $10^3$ (A), $10^4$ (B), $10^5$ (C), $10^6$ (D), $10^7$ (E), respectively.

Calibration Curve Between Bacterial Concentration and AST Time

Figures 10A, 10B, 10C:
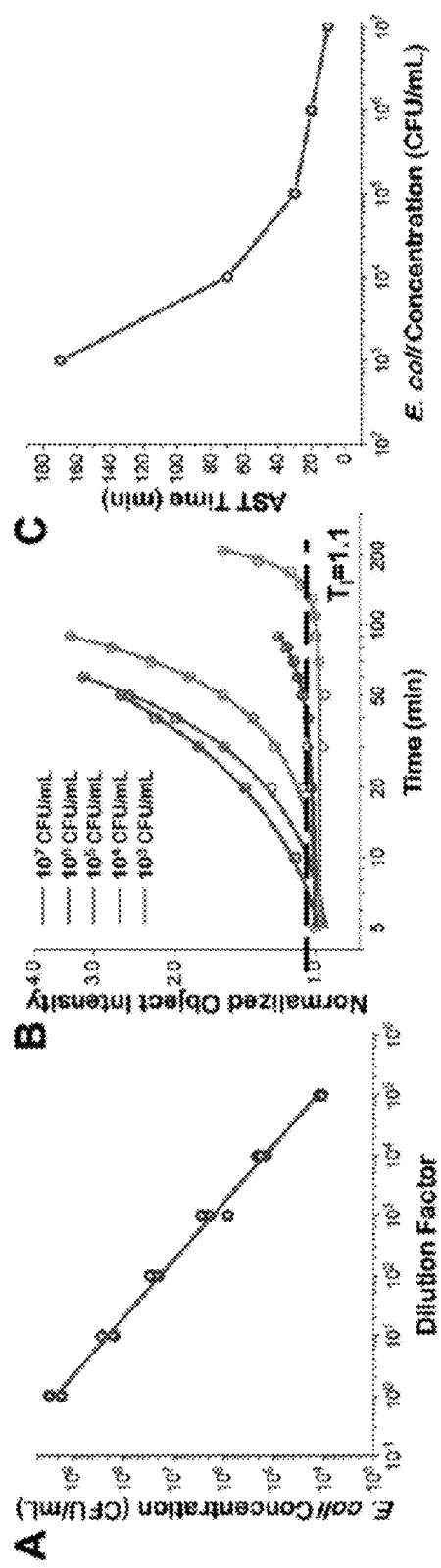
FIGS. 10A-10C are plots showing calibration between bacterial concentration and AST time.

FIGS. 10A-10C are plots showing calibration between bacterial concentration and AST time. A. The plating validation of initial *E. coli* concentrations at different dilutions. B. The bacterial growth curve of different cell concentrations ($10^3$-$10^7$ CFU/ml) with and without antibiotics. C. The calibration curve between bacterial concentration and AST time. The threshold for AST time is set at 1.1 as in B.

Figures 11A, 11B:
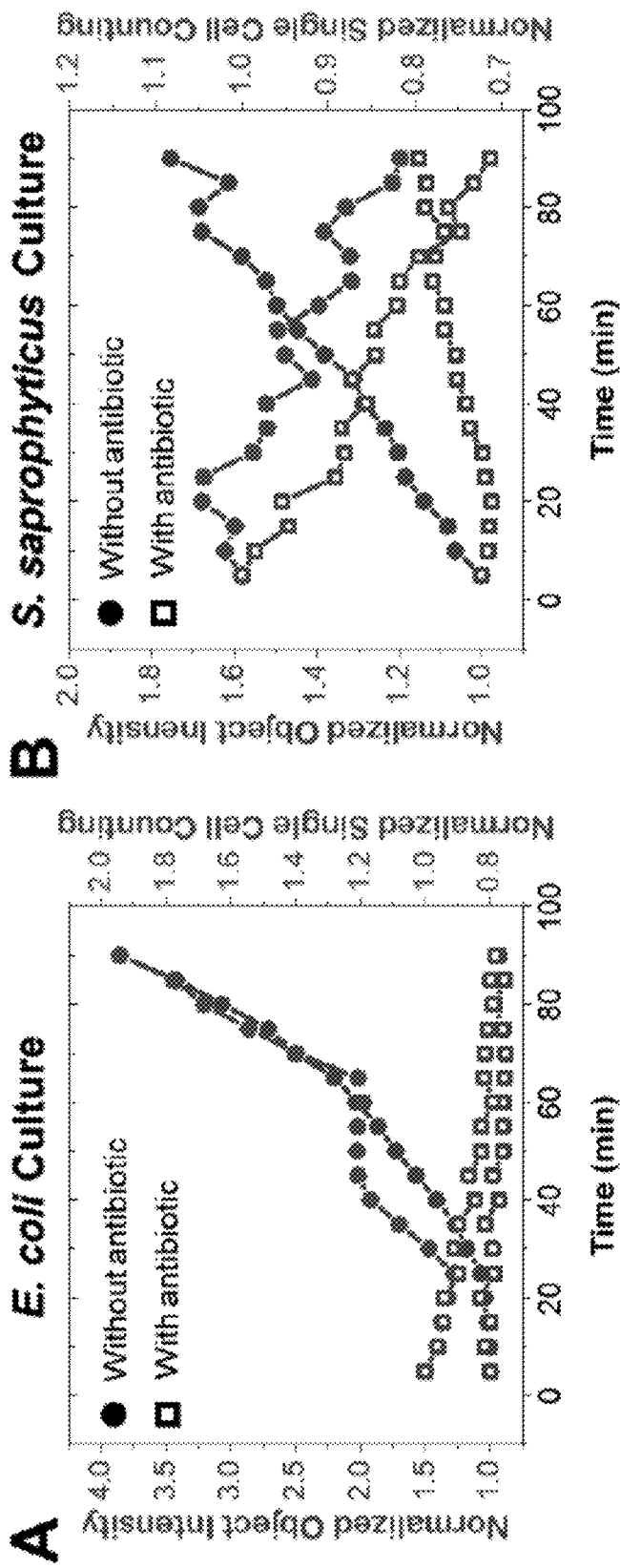
FIGS. 11A-11B are plots showing representative results of object intensity detection and digital counting for pure *E. coli* (A) and *Staphylococcus* sample (B).

Comparison of Object Intensity Detection and Digital Counting for Pure *E. coli* and *Staphylococcus* Sample FIGS. 11A-11B are plots showing representative results of object intensity detection and digital counting for pure *E. coli* (A) and *Staphylococcus* sample (B). Digital counting only works with *E. coli*, while object intensity works with both stains.

Initial Sample Validation Results

On-site initial bacterial load validation is performed with sample plating and colony counting. Upon urine sample reception, samples were subjected to serial dilutions and plated on LB agar for colony enumeration. This plating validation provides initial bacterial concentration references and reveals any viability changes during sample storage and transportation. While 66 of 130 clinical samples were confirmed to have greater than $10^3$ bacterial cells per mL, two of these contained concentrations below the clinical threshold of $10^4$ CFU/mL, and six had bacterial concentrations that were 10-100 times less than those initially determined by Mayo Clinic (FIG. 12), before storage and transport. Therefore, we anticipate greater accuracy when rapid AST is performed in POC settings and this loss in bacterial viability is avoided.

Figure 12:
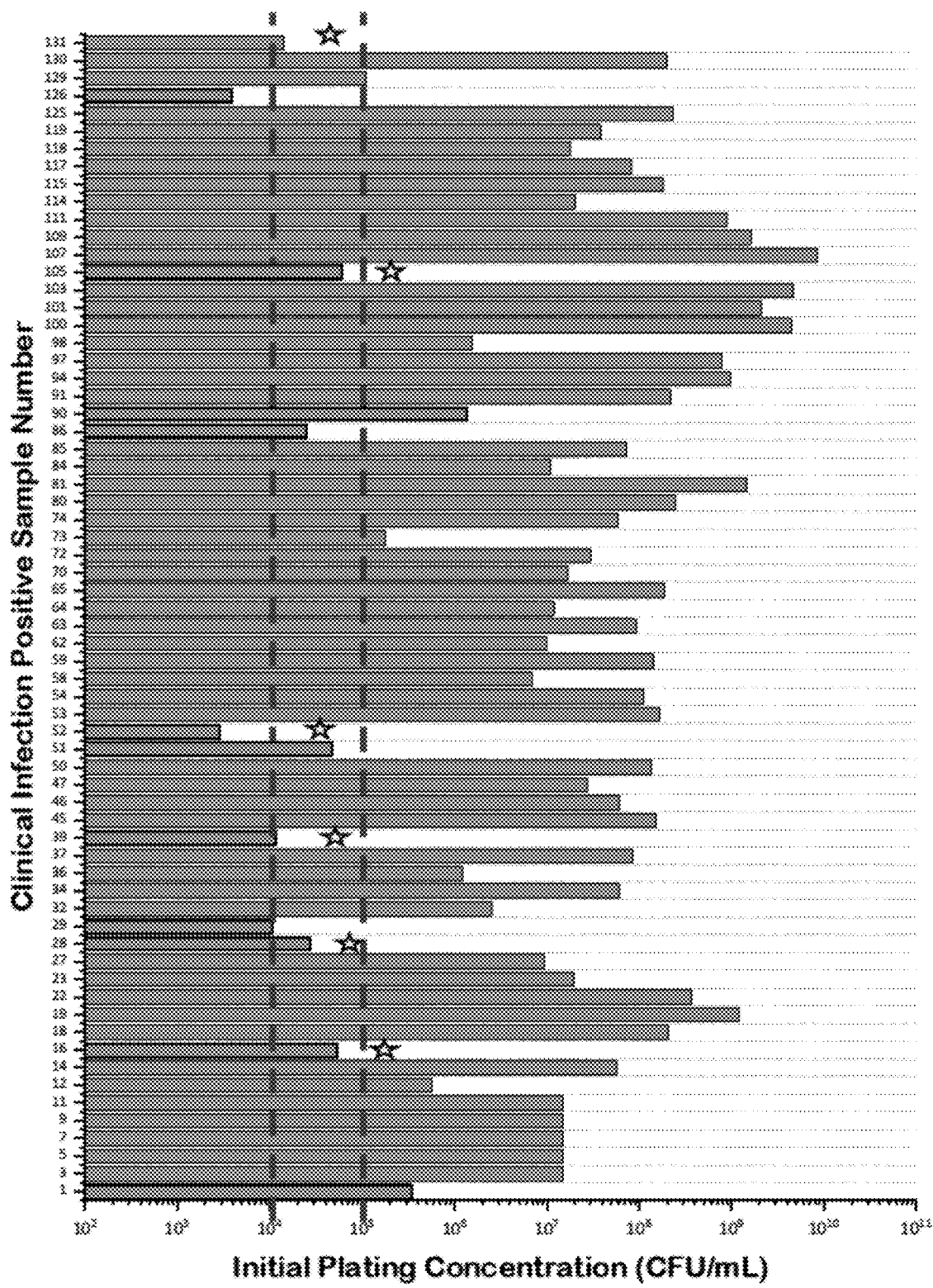
FIG. 12 is a plot showing initial plating validation of all 66 clinically determined positive sample.

FIG. 12 is a plot showing initial plating validation of all 66 clinically determined positive sample. The bars outlined in black show the initial bacterial concentration of 11 false negative samples. The dashed lines indicate the clinical infection threshold ($10^4$-$10^5$ CFU/mL). The stars indicate the urine samples with initial plating concentrations less than those determined by Mayo Clinic (prior to storage and transport).

Initial and Parallel Plating Validation Result of 11 False Negative Samples

Parallel plating validation was performed along with LVSi detection to test the diluted samples. Both the initial plating and parallel plating results of 11 false negatives samples are presented here. Among the 11 false negative samples, 2 samples were tested negative with the initial on-site plating validation, which is likely due to lost in viability during the cold storage and transportation. The other 9 samples were tested marginal positive with the initial plating (7 out of the 9 samples with concentrations between $10^4$-$10^5$ CFU, and only two of the samples have bacterial concentration higher than $10^5$ CFU), but the parallel plating validation results after all sample handling, including pre-warm, filtration and dilutions show low initial counts of bacterial cells (below 1000 cells/ml) Therefore, most of these false negative results (9/11) are due to low initial bacterial concentration and sample handing process, possibly resulted from over filter or over dilution. These sample were diluted from 10 to 1000 times so that both digital counting and object scattering intensity can be performed. Since OSID-AST can work with much higher particle concentration range, these false negative results could be avoided with less dilution of the sample and better sample collection and handling process.

Figure 13:
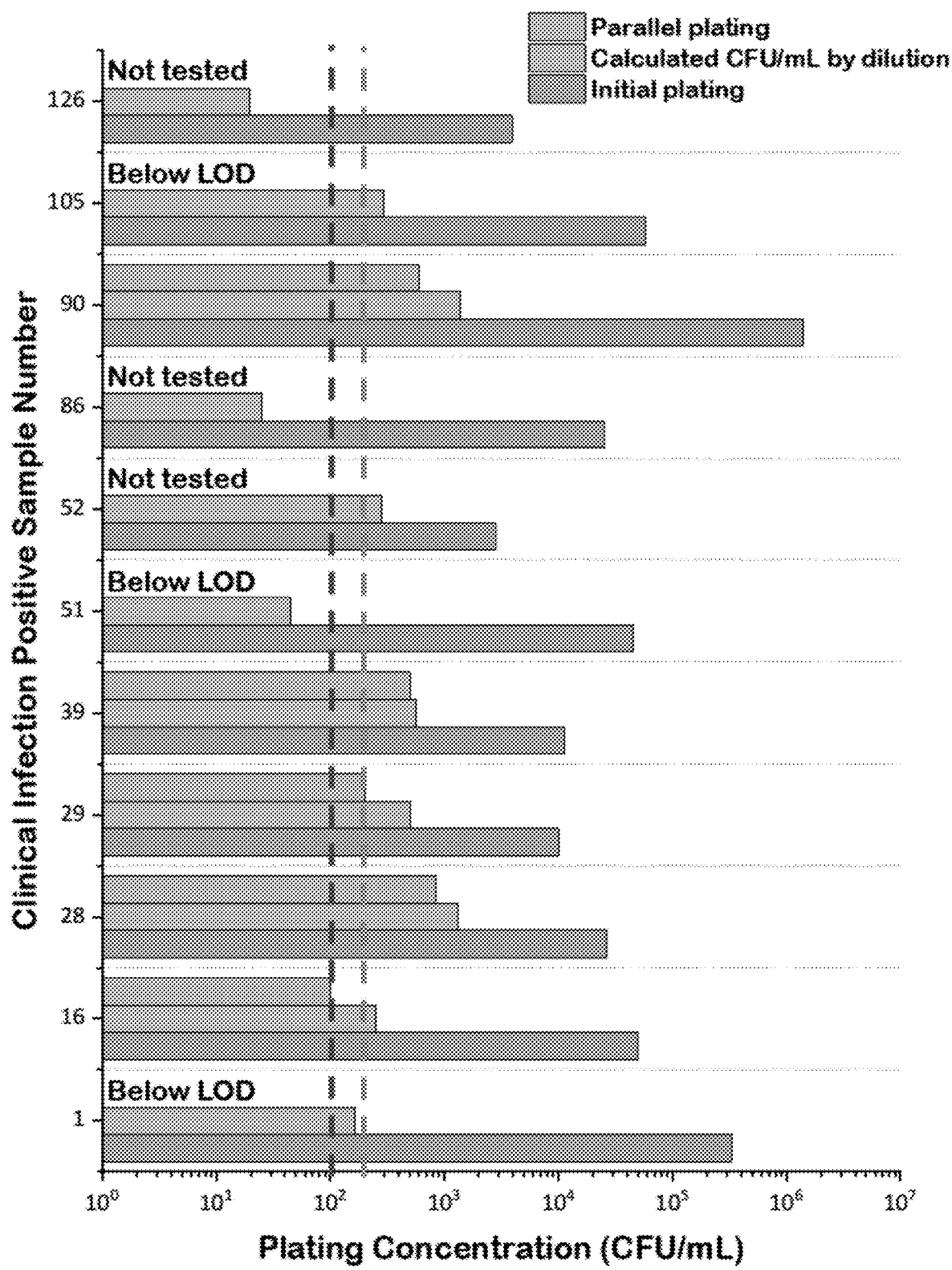
FIG. 13 is a plot showing the comparison of initial plating, calculated CFU/mL by dilution, and the parallel plating results of 11 false negatives samples.

FIG. 13 is a plot showing the comparison of initial plating, calculated CFU/mL by dilution, and the parallel plating results of 11 false negatives samples. The plating results are the mean value of three replicates. The limit of detection (LOD, hatched line on the left) for initial plating is 100 CFU/mL. The limit of detection (LOD, hatched line on the right) for parallel plating is 200 CFU/mL. When parallel plating was performed but colonies were not detected in all three replicates (sample #1, #51, #105), the samples are marked as 'Below LOD'.

Example of False Negative Sample by Counting, Positive by Intensity

In this study, we also measured the same samples with single cell counting method, which needs extra manual cell detection and tracking processing. The single cell counting detection showed 17 false negative samples in the 130 tested samples, with an extra of 6 false negative samples than the object intensity detection. Two of the examples are presented here. This is because object intensity measures both size and number increase during cell grow, while cell counting only signals the number increase, and the number increases always happen later than the size increases.

Figures 14A, 14B:
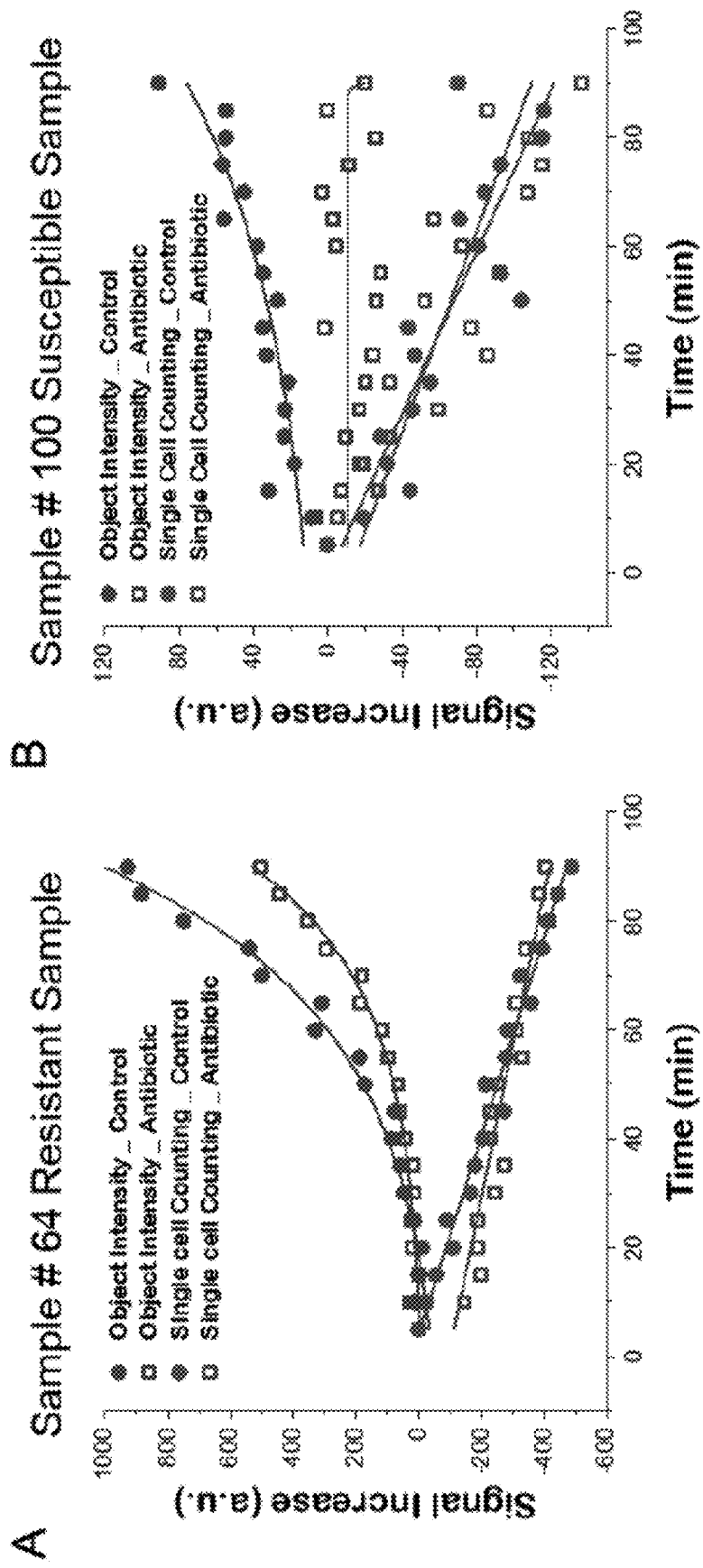
FIGS. 14A-14B are plots showing two of the false negative examples determined by counting, which is determined positive by object intensity detection. A. A resistant sample example. B. A susceptible sample example.

FIGS. 14A-14B are plots showing two of the false negative examples determined by counting, which is determined positive by object intensity detection. A. A resistant sample example. B. A susceptible sample example.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A method of assessing the presence of microbes in a liquid sample, the method comprising:
    directing light from a light source toward a reservoir containing the liquid sample;
    obtaining, with a video camera, a series of images of the liquid sample over a length of time, wherein incident light from the light source is prevented from directly entering the camera, and objects in the liquid sample appear as bright spots in the images of the sample;
    removing background noise from the images of the liquid sample to yield modified images of the sample, wherein removing the background noise comprises averaging frames of raw images to reduce noise and data size to produce a local stack average, subtracting a stack local minimal from the local stack average to remove static and drifting background noises to produce a subtracted stack local minimal, subtracting a stack median of all frames from the subtracted stack local minimal to remove dynamic background noises to produce a median subtracted stack local minimal, and subtracting a local spatial background from the median subtracted stack local minimal to remove spatial optical noises to produce the modified images of the sample;
    assessing, from the modified images of the liquid sample, an initial integrated scattering intensity of the objects ($I_{C0}$) and an integrated scattering intensity of the objects at a time t ($I_{Ct}$); and
    identifying the sample as comprising microbes for ($I_{Ct}$)/($I_{C0}$) above a predefined infection threshold $T_I$, wherein a portion of the sample comprising microbes is treated with an antibiotic to yield a treated liquid sample.

2. The method of claim 1, further comprising:
    directing light from the light source or an additional light source toward an additional reservoir containing the treated liquid sample;
    obtaining, with the video camera or an additional camera, a series of images of the treated liquid sample over the length of time, wherein incident light from the light source or the additional light source, respectively, is prevented from directly entering the camera or the additional camera, respectively, and objects in the treated liquid sample appear as bright spots in the images of the treated liquid sample;
    removing background noise from the images of the treated liquid sample to yield modified images of the treated liquid sample, wherein removing the background noise comprises averaging frames of raw images to reduce noise and data size to produce a local stack average, subtracting a stack local minimal from the local stack average to remove static and drifting background noises to produce a subtracted stack local minimal, subtracting a stack median of all frames from the subtracted stack local minimal to remove dynamic background noises to produce a median subtracted stack local minimal, and subtracting a local spatial background from the median subtracted stack local minimal to remove spatial optical noises to produce the modified images of the treated liquid sample;
    assessing, from the modified images of the treated liquid sample, a change in integrated scattering intensity of the objects in the treated liquid sample from time $t_1$ to time $t_2$ ($\Delta I_{ABX} = I_{ABXt1} - I_{ABXt2}$); and
    assessing, from the modified images of the liquid sample, a change in integrated scattering intensity of the objects in the sample from time $t_1$ to time $t_2$ ($\Delta I_C = I_{Ct1} - I_{Ct2}$).

3. The method of claim 2, further comprising identifying the microbes as resistant to the antibiotic for a ratio of $\Delta I_{ABX}$ to $\Delta I_C$ that exceeds a predefined resistant threshold $T_R$.

4. The method of claim 2, further comprising identifying the microbes as susceptible to the antibiotic for a ratio of $\Delta I_{ABX}$ to $\Delta_{IC}$ that is less than or equal to a predefined resistant threshold $T_R$.

5. The method of claim 1, wherein the microbes comprise bacteria.

6. The method of claim 1, wherein the liquid sample comprises urine.

7. The method of claim 1, wherein the length of time is at least 60 minutes.

8. The method of claim 1, wherein the light source comprises a light emitting diode (LED).

9. The method of claim 1, wherein a volume of the liquid sample is in a range between 1 µL and 10 µL.

10. The method of claim 1, further comprising magnifying the objects in the liquid sample in a range of 1X-5X before obtaining the series of images.

11. The method of claim 1, further comprising maintaining a temperature of the liquid sample between about 35° C. and about 37° C. while obtaining the series of images.

* * * * *